US009487574B2

(12) United States Patent
Carmon

(10) Patent No.: US 9,487,574 B2
(45) Date of Patent: Nov. 8, 2016

(54) ANTIGEN SPECIFIC MULTI EPITOPE VACCINES

(75) Inventor: Lior Carmon, Tel Aviv (IL)

(73) Assignee: VAXIL BIOTHERAPEUTICS LTD., Rehovot (IL)

( * ) Notice: Subject to any disclaimer, the term of this patent is extended or adjusted under 35 U.S.C. 154(b) by 320 days.

(21) Appl. No.: 12/442,495

(22) PCT Filed: Sep. 23, 2007

(86) PCT No.: PCT/IL2007/001168
§ 371 (c)(1),
(2), (4) Date: Nov. 11, 2009

(87) PCT Pub. No.: WO2008/035350
PCT Pub. Date: Mar. 27, 2008

(65) Prior Publication Data
US 2010/0074925 A1    Mar. 25, 2010

Related U.S. Application Data

(60) Provisional application No. 60/846,087, filed on Sep. 21, 2006.

(51) Int. Cl.
*A61K 39/00* (2006.01)
*C07K 14/74* (2006.01)
*C07K 14/47* (2006.01)

(52) U.S. Cl.
CPC ..... *C07K 14/70539* (2013.01); *C07K 14/4727* (2013.01); *C07K 14/4748* (2013.01); *A61K 39/00* (2013.01)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,837,028 A | 6/1989 | Allen | |
| 7,528,224 B1 | 5/2009 | Brossart et al. | |
| 2007/0054262 A1* | 3/2007 | Baker et al. | 435/5 |

FOREIGN PATENT DOCUMENTS

| | | |
|---|---|---|
| WO | 9500159 | 1/1995 |
| WO | 0006723 | 2/2000 |
| WO | 0063363 | 10/2000 |
| WO | 0118035 | 3/2001 |
| WO | 0182963 | 11/2001 |
| WO | 2004022709 | 3/2004 |
| WO | 2005019269 | 3/2005 |
| WO | 2005025612 | 3/2005 |
| WO | WO 2005/025612 * | 3/2005 |
| WO | WO 2006/105448 A2 * | 10/2006 |

OTHER PUBLICATIONS

Alexander et al (J of Immunology, 2002, 168:6189-6198).*
Grant (2002, Synthetic peptides for Production of Antibodies that Recognize Intact Proteins; Current Protocols in Protein Science, 28:18.3:18.3.1-18.3.19).*
Biddison and Martin (Current Protocols in Immunology, 2000, A.1I.1-A.1I.7).*
International Search Report for PCT/IL2007/001168, Completed by the European Patent Office on Jan. 16, 2008, 5 Pages.
Boel et al. Immunity Feb. 1995, vol. 2, p. 167-175, "BAGE: a New Gene Encoding an Antigen Recognized on Human Melanomas by Cytolytic T Lymphocytes."
Brossart et al. Blood Jun. 15, 1999, vol. 93, No. 12, p. 4309-4317, "Identification of HLA-A2-Restricted T-Cell Epitopes Derived From the MUC1 Tumor Antigen for Broadly Applicable Therapies."
Carmon et al. Int. J. Cancer 2000, vol. 85, p. 391-397, "Novel Breast-Tumor-Associated MUC1-Derived Peptides: Characterization in Db-/-X B2 Microglobulin (B2m) Null Mice Transgenic for a Chimeric HLA-A2.1/Db-B2 Microglobulin Single Chain."
Chaux et al. J. Exp. Med. Mar. 1, 1999, vol. 189, No. 5, p. 767-777, "Identification of MAGE-3 Epitopes Presented by HLA-DR Molecules to CD4+ T Lymphocytes."
Touloukian et al. J. Immunol. Apr. 1, 2000, vol. 164, No. 7, p. 3535-3542, "Identiciation of a MHC Class II-Restricted Human gp100 Epitope Using DR4-IE Trnasgenic Mice."
Fisk et al. J. Exp. Med. Jun. 1995, vol. 181, p. 2109-2117, "Identification of an Immunodominant Peptide of HER-2/eu Protooncogene Recognized by Ovariam Tumor-Specific Cytotoxic T Lymphocyte Lines."
Fung et al. Cancer Research 1991, vol. 51,p. 1170-1176, "Specific Immunosuppressive Activity of Epiglycanin, a Mucin-like Glycoprotein Secreted by a Murine Mammary Adenocarcinoma (TA3-HA)."
Gilboa. Nature Reviews Cancer May 2004, vol. 4, p. 401-411, "The promise of cancer vaccines."

(Continued)

*Primary Examiner* — Laura B Goddard
(74) *Attorney, Agent, or Firm* — Susanne M. Hopkins; Roberts Mlotkowsi Safran Cole & Calderon P.C

(57) ABSTRACT

The present invention relates to cancer vaccines composed of the signal peptide domain of tumor associated antigens or proteins. The peptide vaccines of the invention are characterized by having multiple MHC class I and class II epitopes which are highly abundant in the population. Therefore, these vaccines are likely to induce a strong, comprehensive immune response against the target proteins in the majority of the vaccinated population, and thereby induce an immune reaction against tumors expressing such target proteins. Specifically, the invention relates to peptide vaccines composed of the signal peptide domain of Mucin (MUC1), BAGE-1 or ARMET, and their use for the treatment of cancers which express Mucin (MUC1), BAGE-1 or ARMET.

13 Claims, 2 Drawing Sheets

(56) References Cited

OTHER PUBLICATIONS

Graham et al. Cancer Immunol. Immunother. 1996, vol. 42, p. 71-80, "The polymorphic epithelial mucin: potential as an immunogen for a cancer vaccine."
Grulich et al. Lancet 2007, vol. 370, p. 59-67, "Incidence of cancers in people with HIV/AIDS compared with immunosuppressed transplant receipients: a meta-analysis."
Green et al. Cell Mar. 1982, vol. 28, p. 477-487, "Immunogenic Structure of the Influenza Virus Hemagglutinin."
He et al. Cancer Gene Therapy 2003, vol. 10, p. 669-677, "Enhanced tumor immunogenicity through coupling cytokine expression with antigen presentation."
Ho et al. Cancer Research 1993, vol. 53, p. 641-651, "Heterogeneity of Mucin Gene Expression in Normal and Neoplastic Tissues."
Hung et al. J. Exp. Med. Dec. 21, 1998, vol. 188, No. 12, p. 2357-2368, "The Central Role of CD4+T Cells in the Antitumor Immune Response."
Jaeger et al. Int. J. Cancer 1996, vol. 66, p. 162-169, "Generation of Cytotoxic T-Cell Responses with Synthetic Melanoma-Associated Peptides in Vivo: Implications for Tumor Vaccines with Melanoma-Associated Antigens."
Kast et al. Journal of Immunology 1994, vol. 152, p. 3904-3912, "Role of HLA-A Motifs in Identification of Potential CTL Epitopes in Human Papillomavirus Type 16 E6 and E7 Proteins."
Kedar et al. Advances in Cancer Research 1992, vol. 59, p. 245-322, "Cancer Immunotherapy: Are the Results Discouraging? Can They be Improved?"
Knutson et al. The Journal of Clinical Investigation Feb. 2001, vol. 107, No. 4, p. 477-484, "Immunization with a HER-2/neu helper peptide vaccine generates HER-2/eu CD8 T-Cell Immunity in cancer patients."
Lenstra et al. Arch. Virol. 1990, vol. 110, p. 1-24, "Mapping of viral epitopes with prokaryotic expression products."
Lipman et al. Science Mar. 22, 1985, vol. 227, p. 1435-1441, "Rapid and Sensitive Protein Similarity Searches."
Mandelbolm et al. Nature May 5, 1994, vol. 369, p. 67-71, "CTL induction by a tumour-associated antigen octapeptide derived from a murine lung carcinoma."
Mandelboim et al. Nature Medicine Nov. 1995, vol. 1, No. 11, p. 1179-1183, "Regression of established murine carcinoma metastases following vaccination with tumor-associated antigen peptides."
Manici et al. J. Exp. Med. Mar. 1, 1999, vol. 189, No. 5, p. 871-876, "Melanoma Cells Present a MAGE-3 Epitope to CD4+ Cytotoxic T Cells is Association with Histocompatibility Leukocyte Antigen DR11."
Marchand et al. Int. J. Cancer. 1995, vol. 63, p. 883-885, "Letter to the Editor, Tumor regression responses in melanoma patients treated with a peptide encoded by gene MAGE-3."
McGuckin et al. Human Pathology Apr. 1995, vol. 26, No. 4, p. 432-439, "Prognostic Significance of MUC1 Epithelial Mucin Expression in Breast Cancer."
Minev et al. Eur. J. Immunol. 2000, vol. 30, p. 2115-2124, "Synthetic insertion signal sequences enhance MHC class I presentation of a peptide from the melanoma antigen MART-1."
Morein et al. Nature Mar. 29, 1984, vol. 308, p. A57-460, "Iscom, a novel structure for antigenic presentation of membrane proteins from enveloped viruses."
Pardoll et al. Curr. Opin. Immunol. 1998, vol. 10, p. 588-594, "The role of CD4+ T cell responses in antitumor immunity."
Rammensee et al. Annu. Rev. Immunol. 1993, vol. 11, p. 213-244, "Peptides Naturally Presented by MHC Class I Molecules."
Ras et al. Human Immunology 1997, vol. 53, p. 81-89, "Identification of Potential HLA-A 0201 Restricted CTL Epitopes Derived from the Epithelial Cell Adhesion Molecule (Ep-CAM) and the Carcinoembryonic Antigen (CEA)."
Rhodes et al. Nature Genetics Supplement Jun. 2005, vol. 37, p. S31-S37, "Integrative analysis of the cancer transcriptome."
Rosenberg et al. Nat. Med. Mar. 1998, vol. 4, No. 3, p. 321-327, "Immunologic and therapeutic evaluation of a synthetic peptide vaccine for the treatment of patients with metastatic melanoma."
Rosenberg et al. Nat. Med. Sep. 2004, vol. 10, No. 9, p. 909-915, "Cancer immunotherapy: moving beyond current vaccines."
Sherritt et al. International Immunology 2000, vol. 13, No. 3, p. 265-271, "Immunization with tumor-associated epitopes fused to an endoplasmic reticulum translocation signal sequence affords protection against tumors with down-regulated expression of MHC and peptide transporters."
Shridhar et al. Cancer Res. 1996, vol. 56, p. 5576-5578, "Mutations in the Arginine-rich Protein Gene, in Lung, Breast, and Prostate Cancers, and in Squamous Cell Carcinoma of the Head and Neck."
Townsend et al. Ann. Rev. Immunol. 1989, vol. 7, p. 601-624, "Antigen Recognition by Class I-Restricted T Lymphocytes."
Treon et al. Blood 2000, vol. 96, p. 3147-3153, "Elevated soluble MUC1 levels and decreased anti-MUC1 antibody levels in patients with multiple myeloma."
Weber et al. Journal of Immunotherapy 1999, vol. 22, No. 5, p. 431-440, "A Phase I Trial of an HLA-A1 Restricted MAGE-3 Epitope Peptide with Incomplete Freund's Adjuvant in Patients with Resected High-Risk Melanoma."
Wu et al. The Journal of Immunology Mar. 1, 1992, vol. 148, No. 5, p. 1519-1525, "Saponin Adjuvant Enhancement of Antigen-Specific Immune Responses to an Experimental HIV-1 Vaccine."
Jiang et al. Infection and immunity Jul. 2002, vol. 70, No. 7, p. 3539-3545, "Role of Signal Sequence in Vaccine-Induced Protection against Experimental Coccidioidomycosis."
Wierecky et al. Cancer Res Jun. 1, 2006, vol. 66, No. 11, p. 5910-5918, "Immunologic and Clinical Responses after Vaccinations with Peptide-Pulsed Dendritic Cells in Metastatic Renal Cancer Patients."
Pinchuk et al. The Journal of Immunology May 2005, vol. 174, No. 9, p. 5729-5739, "A CD8+ T Cell Heptaepitope Minigene Vaccine Induces Protective Immunity against Chlamydia pneumoniae."
Gunnar Von Heijne. Subcellular Biochemistry 1994, vol. 22, 22 Pages, "Signals for Protein Targeting into and across Membranes."
Marchand et al. Int. J. Cancer 1999, vol. 80, p. 219-231, "Tumor Regressions Observed in Patients with Metastatic Melanoma Treated with an Antigenic Petide Encoded by Gen Mage-3 and Presented by HLA-A1."
Kovjazin et al. Vaccine 2011, vol. 29, p. 4676-4686, "ImMucin: A novel therapeutic vaccine with promiscuous MHC binding for the treatment of MUC1-expressing tumors."
Kovjazin et al. Mol. Immunol. Apr. 2011, vol. 48, No. 8, p. 1009-1018, "Signal Peptides and Trans-membrane Regions are Broadly Immunogenic and have High CD8+ T Cell Epitope Densities: Implications for Vaccine Development."
Kovjazin, R. et al., "The use of signal peptide domains as vaccine candidates", Human Vaccines & Immunotherapeutics, Oct. 1, 2014, 8 pgs., vol. 10 Issue 9.
Carmon et al. British Journal of Haematology Dec. 11, 2014, vol. 168, Issue 1, p. 1-13, "Phase I/II study exploring ImMucin, a pan-major histocompatibility complex, anti-MUC1 signal peptide vaccine, in multiple myeloma patients".

* cited by examiner

```
SEQUENCE LISTING

<160> NUMBER OF SEQ ID NOS: 39

<210> SEQ ID NO 1
<211> LENGTH: 21
<212> TYPE: PRT
<213> ORGANISM: Homo sapiens

<400> SEQUENCE: 1

Met Trp Ala Thr Gln Gly Leu Ala Val Ala Leu Ala Leu Ser Val Leu
1               5                   10                  15

Pro Gly Ser Arg Ala
            20

<210> SEQ ID NO 2
<211> LENGTH: 27
<212> TYPE: PRT
<213> ORGANISM: Homo sapiens

<400> SEQUENCE: 2

Met Leu Arg Leu Pro Thr Val Phe Arg Gln Met Arg Pro Val Ser Arg
1               5                   10                  15

Val Leu Ala Pro His Leu Thr Arg Ala Tyr Ala
            20                  25

<210> SEQ ID NO 3
<211> LENGTH: 20
<212> TYPE: PRT
<213> ORGANISM: Homo sapiens

<400> SEQUENCE: 3

Met Glu Gly Lys Trp Leu Leu Cys Met Leu Leu Val Leu Gly Thr Ala
1               5                   10                  15

Ile Val Glu Ala
            20

<210> SEQ ID NO 4
<211> LENGTH: 35
<212> TYPE: PRT
```

<213> ORGANISM: Homo sapiens

<400> SEQUENCE: 4

Met Ala Ala Thr Ser Leu Met Ser Ala Leu Ala Ala Arg Leu Leu Gln
1               5                   10                  15

Pro Ala His Ser Cys Ser Leu Arg Leu Arg Pro Phe His Leu Ala Ala
            20                  25                  30

Val Arg Asn
        35

<210> SEQ ID NO 5
<211> LENGTH: 24
<212> TYPE: PRT
<213> ORGANISM: Homo sapiens

<400> SEQUENCE: 5

Met Lys Thr Trp Val Lys Ile Val Phe Gly Val Ala Thr Ser Ala Val
1               5                   10                  15

Leu Ala Leu Leu Val Met Cys Ile
            20

<210> SEQ ID NO 6
<211> LENGTH: 19
<212> TYPE: PRT
<213> ORGANISM: Homo sapiens

<400> SEQUENCE: 6

Met Ser Leu Trp Gln Pro Leu Val Leu Val Leu Leu Val Leu Gly Cys
1               5                   10                  15

Cys Phe Ala

<210> SEQ ID NO 7
<211> LENGTH: 17
<212> TYPE: PRT
<213> ORGANISM: Homo sapiens

<400> SEQUENCE: 7

Met Ala Ala Arg Ala Val Phe Leu Ala Leu Ser Ala Gln Leu Leu Gln
1               5                   10                  15

Ala

<210> SEQ ID NO 8
<211> LENGTH: 26
<212> TYPE: PRT
<213> ORGANISM: Homo sapiens

<400> SEQUENCE: 8

Met Ala Leu Phe Thr Pro Trp Lys Leu Ser Ser Gln Lys Leu Gly Phe
1               5                   10                  15

Phe Leu Val Thr Phe Gly Phe Ile Trp Gly
            20                  25

<210> SEQ ID NO 9
<211> LENGTH: 19
<212> TYPE: PRT
<213> ORGANISM: Homo sapiens

<400> SEQUENCE: 9

Met Asn Phe Tyr Leu Leu Leu Ala Ser Ser Ile Leu Cys Ala Leu Ile
1               5                   10                  15

Val Phe Trp

<210> SEQ ID NO 10
<211> LENGTH: 21
<212> TYPE: PRT
<213> ORGANISM: Homo sapiens

<400> SEQUENCE: 10

Met Thr Pro Gly Thr Gln Ser Pro Phe Phe Leu Leu Leu Leu Leu Thr
1               5                   10                  15

Val Leu Thr Val Val
            20

<210> SEQ ID NO 11
<211> LENGTH: 34
<212> TYPE: PRT
<213> ORGANISM: Homo sapiens

<400> SEQUENCE: 11

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala

<210> SEQ ID NO 12
<211> LENGTH: 23
<212> TYPE: PRT
<213> ORGANISM: Homo sapiens

<400> SEQUENCE: 12

Met Asp Leu Val Leu Lys Arg Cys Leu Leu His Leu Ala Val Ile Gly
1               5                   10                  15

Ala Leu Leu Ala Val Gly Ala
            20

<210> SEQ ID NO 13
<211> LENGTH: 26
<212> TYPE: PRT
<213> ORGANISM: Homo sapiens

<400> SEQUENCE: 13

Met Ala Thr Ala Gly Asn Pro Trp Gly Trp Phe Leu Gly Tyr Leu Ile
1               5                   10                  15

Leu Gly Val Ala Gly Ser Leu Val Ser Gly
            20                  25

<210> SEQ ID NO 14
<211> LENGTH: 18
<212> TYPE: PRT
<213> ORGANISM: Homo sapiens

<400> SEQUENCE: 14

Met Lys Leu Leu Met Val Leu Met Leu Ala Ala Leu Ser Gln His Cys
1               5                   10                  15

Tyr Ala

<210> SEQ ID NO 15
<211> LENGTH: 50
<212> TYPE: PRT
<213> ORGANISM: Homo sapiens

<400> SEQUENCE: 15

```
Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
                20                  25                  30

Leu Thr Val Ile Leu Gly Val Leu Leu Ile Gly Cys Trp Tyr Cys
        35                  40                  45

Arg Arg
    50

<210> SEQ ID NO 16
<211> LENGTH: 48
<212> TYPE: PRT
<213> ORGANISM: Homo sapiens

<400> SEQUENCE: 16

Met Ala Ser Pro Arg Leu Gly Thr Phe Cys Cys Pro Thr Arg Asp Ala
1               5                   10                  15

Ala Thr Gln Leu Val Leu Ser Phe Gln Pro Arg Ala Phe His Ala Leu
                20                  25                  30

Cys Leu Gly Ser Gly Gly Leu Arg Leu Ala Leu Gly Leu Leu Gln Leu
        35                  40                  45

<210> SEQ ID NO 17
<211> LENGTH: 17
<212> TYPE: PRT
<213> ORGANISM: Homo sapiens

<400> SEQUENCE: 17

Met Trp Val Pro Val Val Phe Leu Thr Leu Ser Val Thr Trp Ile Gly
1               5                   10                  15

Ala

<210> SEQ ID NO 18
<211> LENGTH: 24
<212> TYPE: PRT
<213> ORGANISM: Homo sapiens

<400> SEQUENCE: 18

Met Ser Ala Pro Lys Leu Leu Ser Leu Gly Cys Ile Phe Phe Pro Leu
1               5                   10                  15

Leu Leu Phe Gln Gln Ala Arg Ala
                20

<210> SEQ ID NO 19
<211> LENGTH: 17
<212> TYPE: PRT
<213> ORGANISM: Homo sapiens

<400> SEQUENCE: 19

Met Leu Leu Ala Val Leu Tyr Cys Leu Leu Trp Ser Phe Gln Thr Ser
1               5                   10                  15

Ala

<210> SEQ ID NO 20
<211> LENGTH: 17
<212> TYPE: PRT
<213> ORGANISM: Homo sapiens

<400> SEQUENCE: 20

Met Ser Leu Ser Phe Leu Leu Leu Leu Phe Phe Ser His Leu Ile Leu
```

Ser

<210> SEQ ID NO 21
<211> LENGTH: 22
<212> TYPE: PRT
<213> ORGANISM: Homo sapiens

<400> SEQUENCE: 21

Met Glu Leu Ala Ala Leu Cys Arg Trp Gly Leu Leu Leu Ala Leu Leu
1               5                   10                  15

Pro Pro Gly Ala Ala Ser
            20

<210> SEQ ID NO 22
<211> LENGTH: 18
<212> TYPE: PRT
<213> ORGANISM: Homo sapiens

<400> SEQUENCE: 22

Met Lys Trp Val Glu Ser Ile Phe Leu Ile Phe Leu Leu Asn Phe Thr
1               5                   10                  15

Glu Ser

<210> SEQ ID NO 23
<211> LENGTH: 29
<212> TYPE: PRT
<213> ORGANISM: Homo sapiens

<400> SEQUENCE: 23

Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala
            20                  25

<210> SEQ ID NO 24
<211> LENGTH: 40
<212> TYPE: PRT
<213> ORGANISM: Homo sapiens

<400> SEQUENCE: 24

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly
            35                  40

<210> SEQ ID NO 25
<211> LENGTH: 23
<212> TYPE: PRT
<213> ORGANISM: Homo sapiens

<400> SEQUENCE: 25

Met Pro Arg Ala Pro Arg Cys Arg Ala Val Arg Ser Leu Leu Arg Ser
1               5                   10                  15

His Tyr Arg Glu Val Leu Pro
            20

<210> SEQ ID NO 26
<211> LENGTH: 27

<212> TYPE: PRT
<213> ORGANISM: Homo sapiens

<400> SEQUENCE: 26

Met Phe Asp Lys Thr Arg Leu Pro Tyr Val Ala Leu Asp Val Leu Cys
1               5                   10                  15
Val Leu Leu Ala Gly Leu Pro Phe Ala Ile Leu
            20                  25

<210> SEQ ID NO 27
<211> LENGTH: 25
<212> TYPE: PRT
<213> ORGANISM: Homo sapiens

<400> SEQUENCE: 27

Met Ala Pro Leu Leu Pro Ile Arg Thr Leu Pro Leu Ile Leu Ile Leu
1               5                   10                  15
Leu Ala Leu Leu Ser Pro Gly Ala Ala
            20                  25

<210> SEQ ID NO 28
<211> LENGTH: 24
<212> TYPE: PRT
<213> ORGANISM: Homo sapiens

<400> SEQUENCE: 28

Met Ala His Arg Pro Pro Ser Pro Ala Leu Ala Ser Val Leu Leu Ala
1               5                   10                  15
Leu Leu Leu Ser Gly Ala Ala Arg
            20

<210> SEQ ID NO 29
<211> LENGTH: 9
<212> TYPE: PRT
<213> ORGANISM: Homo sapiens

<400> SEQUENCE: 29

Leu Leu Leu Thr Val Leu Thr Val Val
1               5

<210> SEQ ID NO 30
<211> LENGTH: 9
<212> TYPE: PRT
<213> ORGANISM: Homo sapiens

<400> SEQUENCE: 30

Leu Leu Leu Leu Thr Val Leu Thr Val
1               5

<210> SEQ ID NO 31
<211> LENGTH: 9
<212> TYPE: PRT
<213> ORGANISM: Homo sapiens

<400> SEQUENCE: 31

Thr Gln Ser Pro Phe Phe Leu Leu Leu
1               5

<210> SEQ ID NO 32
<211> LENGTH: 9
<212> TYPE: PRT
<213> ORGANISM: Homo sapiens

<400> SEQUENCE: 32

```
Ser Pro Phe Phe Leu Leu Leu Leu
1               5

<210> SEQ ID NO 33
<211> LENGTH: 9
<212> TYPE: PRT
<213> ORGANISM: Homo sapiens

<400> SEQUENCE: 33

Phe Leu Leu Leu Leu Leu Thr Val Leu
1               5

<210> SEQ ID NO 34
<211> LENGTH: 9
<212> TYPE: PRT
<213> ORGANISM: Homo sapiens

<400> SEQUENCE: 34

Leu Leu Leu Leu Leu Thr Val Leu Thr
1               5

<210> SEQ ID NO 35
<211> LENGTH: 9
<212> TYPE: PRT
<213> ORGANISM: Homo sapiens

<400> SEQUENCE: 35

Gly Thr Gln Ser Pro Phe Phe Leu Leu
1               5

<210> SEQ ID NO 36
<211> LENGTH: 9
<212> TYPE: PRT
<213> ORGANISM: Homo sapiens

<400> SEQUENCE: 36

Thr Pro Gly Thr Gln Ser Pro Phe Phe
1               5

<210> SEQ ID NO 37
<211> LENGTH: 9
<212> TYPE: PRT
<213> ORGANISM: Homo sapiens

<400> SEQUENCE: 37

Phe Phe Leu Leu Leu Leu Leu Thr Val
1               5

<210> SEQ ID NO 38
<211> LENGTH: 9
<212> TYPE: PRT
<213> ORGANISM: Homo sapiens

<400> SEQUENCE: 38

Met Thr Pro Gly Thr Gln Ser Pro Phe
1               5

<210> SEQ ID NO 39
<211> LENGTH: 9
```

```
<212> TYPE: PRT
<213> ORGANISM: Homo sapiens

<400> SEQUENCE: 39

Gln Ser Pro Phe Phe Leu Leu Leu Leu
1               5
```

ANTIGEN SPECIFIC MULTI EPITOPE VACCINES

CROSS-REFERENCE TO RELATED APPLICATION

This application claims the benefit of U.S. provisional application Ser. No. 60/846,087 filed Sep. 21, 2006.

SEQUENCE LISTING

The text file REIN0119PUSA_ST25.txt, created Mar. 18 2014, and of size 10 KB, filed herewith, is hereby incorporated by reference.

FIELD OF THE INVENTION

The present invention relates to cancer peptide vaccines with pan HLA class I and class II binding properties, as well as to pharmaceutical compositions containing the peptide vaccines and methods for treating or preventing cancer.

INTRODUCTION

Cellular Active Immunotherapy

Widespread metastatic disease is considered by the medical establishment to be incurable, since surgery and radiation are not viable treatments, and response rates with current chemotherapy regimens are low. Also, the toxic side effects of non-specific chemotherapeutic agents often limit the dose that can be administered.

Recent Meta Analysis compared the incidence of cancers in people with HIV/AIDS to these with immunosuppressed transplant recipient and showed similarity of the pattern of increased risk of cancer in the two populations (Grulich et al, 2007) This finding suggests that it is the immune deficiency, rather than other risk factors for cancer, that is responsible for the increased risk in these two patient populations.

Active immunotherapy approaches such as cancer vaccines offer hope for cancer specific therapy that could eradicate metastatic tumor cells from the body to achieve a complete cure (Kedar et al., 1995). The rational behind this strategy is based on the following:

- It is now well established that immune cells, predominantly T lymphocytes, can recognize Tumor Associated Antigens (TAA) and kill tumor cells.
- It is also well appreciated, that cancer cells appear to be fully sensitive to tumor-specific T lymphocytes, suggesting that an anti-tumor vaccination is attainable. (Gilboa E. 2004).

Nevertheless, there are few major differences between therapeutic vaccines such as anti-cancer vaccines and prophylactic (preventive or "conventional") anti-infective vaccines. First, unlike prophylactic vaccines, therapeutic vaccines are generally expected to treat sick individuals, suggesting that a broader and stronger immune response is required. Second, prophylactic vaccines are generally induced against highly immunogenic "foreign" epitopes derived from viruses or bacteria and thus easily induce a strong response with a high number of T cell specific clones. In contrast, therapeutic vaccines in particular cancer vaccines composed of self derived TAAs are less immunogenic and therefore are frequently associated with low or minimal induction of activated T cell clones. Lastly, it is more difficult to induce an effective response in cancer patients, which are, at least temporarily immune-suppressed, than in healthy immune-competent individuals which are the target market of prophylactic vaccines.

For that extent, a desired therapeutic vaccine would need to prime a robust cellular reaction, which will involve multiple clones of T cell lymphocytes predominantly T killer ($CD8^+$) and T Helper ($CD4^+$).

Cancer Vaccines

Strategies in cancer immunization have taken many forms based on the antigen used as the immunogenic determinant. These approaches include, among others, the use of whole tumor cell, tumor cell extraction, purified peptide, protein or DNA of selected TAA/s. The products in development can be divided into two main groups:

1. Vaccines consisting of selected MHC class I-restricted sequences from a certain TAA/s. These vaccines consist of high purity sequence/s resembling immunogenic epitopes of a given TAA/s
2. Vaccines consisting of the entire sequence of a certain TAA/s. In this approach the vaccine is composed of a mixture (at various levels of purity) of immunogenic and non-immunogenic MHC class I-restricted epitopes of a given TAA/s.

Vaccines with Defined Class I Restricted Epitopes

MHC class I-restricted TAA peptides are the targets of Cytotoxic T lymphocytes (CTL), which constitute one of the powerful effectors of the immune system against tumors (Townsend et al., 1989). These peptide vaccines are usually 8 to 10 amino acids (AA) long, with 2 to 3 primary anchor residues that interact with the Major Histocompatibility complex (MHC) class I molecules and 2 to 3 AA residues that engage the T-cell receptor on $CD8^+$ cells (Rammensee et al., 1993). Several methods have been employed to identify tumor associated epitopes. One such method is the identification of $CD8^+$ epitopes subsequent to the search for MHC-binding motifs in known putative TAAs, (Kast et al., 1994) as was shown in the case of the breast-carcinoma-associated HER-2/neu receptor (Fisk et al., 1995) or the colorectal tumor associated Carcino-Embryonic Antigen (CEA) (Ras et al., 1997).

Preclinical evaluation of the isolated MHC class I-restricted TAA peptides manifested promising results both in vitro and in vivo (Mandelboim et al, 1994; Mandelboim et al, 1995). Yet, in spite of the vast preclinical experience gathered over the last two decades, the clinical benefit of these MHC class I-restricted peptide vaccines, (most of which are HLA-2.1-restricted), manifested a low level of response. That is to say, there was moderated improvement in clinical parameters beyond the induction of a measurable immune response (Marchand et al, 1995; Rosenberg et al, 1998; Jaeger et al, 1996 Rosenberg et al, 2004). The main explanations for this outcome are the following:

A. The limited repertoire of anti-tumor $CD8^+$ T cell clones that could be induced against a single MHC-class I restricted immunogenic epitope. Namely, it is most likely that these vaccines are inducing an overall weak response via T cell clones that are restricted merely to a single immunogenic epitope on one MHC class I-restricted allele. Since the abundance of one epitope on tumor cell is limited, the chance of effective immunotherapy is low. In this regards, one also needs to appreciate that vaccines restricted to a single MHC class I allele are applicable only to the specific patients who are positive for the selected allele (up to 35% of the population in case of the most frequent alleles).

B. The lack of $CD4^+$ T cells activation. $CD4^+$ T cell activation is mediated via MHC class II-binding epitopes and is critical for the initiation (priming) and long lasting memory of most immune responses. CD4+ T cells have a key role as effector cells with anti-tumor properties.

The need for CD4+ signal for mounting an effective immunity of CD8+ T cells is a well-documented process known as "immune priming". CD4+ T-cell responses are essential to promote the accumulation of Antigen-Presenting Cells (APC) for effective immune priming (Hung et al. 1998) and also for extending the life of anti-tumor CD8+ T cells i.e. memory response vs. short living response. The limited number of known antigen specific MHC class II epitopes, led in many cases to the administration of MHC class I epitopes with universal non-specific MHC class II restricted epitopes such as the pan-class II epitope peptide PADRE (Weber et al., 1999). Although response against the universal MHC class II-restricted epitopes was increased, elevation in CD8+ T-cell effectors specific to the MHC class I-restricted epitope have been limited (Weber et al., 1999).

Another important feature of CD4+ T cells is their role as effector cells with direct anti-tumor activity (Pardoll and Topalian 1998, Christopher et al., 2000). However, since, unlike MHC class I peptide, MHC class II peptide ligands do not have restricted binding properties, their isolation is more complicated. Thus, successful attempts in this direction were limited and arrived only more recently along with the development of sophisticated in-silico class II prediction software and class II transgenic mice (Chaux et al., 1999; Manici et al., 1999). Nevertheless, selected publications e.g. the isolation of class II epitopes like the HLA-DR13, melanoma-associated MAGE-3 epitope (Chaux et al., 1999) and HLA-DRB1*0401-Restricted Human gp100 (Pardoll and Topalian 1998, Christopher et al., 2000), emphasized the importance of these epitopes for more effective cancer vaccines.

Vaccines Consisting of the Entire TAA or (Non-Defined) Epitopes

The other strategy used to overcome the limited repertoire of anti-tumor CD8+ T cell clones is the use of the entire TAA rather then selecting and defining the only relevant immunodominant epitopes. This strategy is more straightforward, as one does not need to isolate the immunogenic epitopes within a given TAA. However, it may very well lead to the "dilution" of the immunogenic epitopes with less immunogenic epitopes, hence decreasing the level of specific immunity or reduce the repertoire of anti-tumor CD8+ T cell clones. Furthermore, some of these less immunogenic epitopes could potentially induce a status of "Immune Anergy" (non responsiveness) which can potentially lead to a decrease in the intensity of the specific immunity or even to status of autoimmunity.

As for the induction of CD4+ specific response, the majority of these vaccines where not designed with the ability to induce CD4+ response via specific MHC class II epitopes.

Knutson and her colleagues (Knutson et al., 2001) prepared antigen specific MHC class II "helper" peptides which contain encompassed class I binding motifs. In a set of studies, the researchers raised the question whether HER-2/neu-specific CD8+ T-cell immunity could be elicited using HER-2/neu-derived MHC class II "helper" peptides, which contain encompassed HLA-A2-binding motifs. The study was performed on nineteen HLA-A2 patients with HER-2/neu-over expressing cancers. After vaccination, the frequency of peptide-specific T-cell precursors specific to the HLA-A2 peptides increased in the majority of patients. In addition, the peptide-specific T cells were able to lyse tumors. More importantly, the responses lasted for a long time and were detectable for more than a year after the final vaccination in select patients. This study suggested an improved anti-cancer immunity via combination of class-I and class-II epitopes derived from the same TAA.

In summary, cancer therapeutic vaccines are required to be:

Antigen specific to avoid potential Anergy and autoimmunity.

Highly potent in inducing a strong, comprehensive and long lasting response involving CD4+ plus CD8+ T cells.

Applicable in the majority of the target population.

Signal Peptides

Almost half of the proteins of an average cell are translocated across membranes. Proteins directed into the secretory pathway use amino-terminal signal peptides to interact with the translation machinery. The translocation of secretory proteins across intracellular membranes and final localization are mediated by signal peptides (SP) which are 'address tags' contained within their amino acid sequences. Signal peptides, comprising the N-terminal 15-60 amino acids of proteins, are necessary for the translocation across the membrane on the secretory pathway and thus universally control the entry of all proteins both in eukaryotes and prokaryotes to the secretory pathway. Signal peptides generally consist of three parts: an N-terminal region of differing length, which usually comprises positively charged amino acids; a hydrophobic domain; and a short carboxy-terminal peptide segment. In eukaryotes, the signal peptide of a nascent precursor protein (pre-protein) directs the ribosome to the rough Endoplasmic Reticulum (ER) membrane and initiates the transport of the growing peptide chain across it. In prokaryotes, the signal peptide directs the pre-protein to the cytoplasmic membrane. However, the signal peptide is not responsible for the final destination of the mature protein; secretory proteins devoid of further address tags in their sequence are by default secreted to the external environment. Signal peptides are cleaved from precursor proteins by an endoplasmic reticulum (ER)-resident signal peptidase or they remain uncleaved and function as a membrane anchor. During recent years, a more advanced view of signal peptides has evolved, showing that the functions and immunodominance of certain signal peptides are much more versatile than previously anticipated.

Signal Peptides and Elevated Immunity

Selected reports have revealed the advantages of linking signal peptide sequences derived from various origins, to selected immunogenic epitopes. In the context of cancer immunotherapy, research by Sherritt and her colleagues has shown that the linking of signal peptide from the adenovirus E3/19 kDa protein to several murine melanoma associate epitopes results in a superior production of CTL as well as in better CTL mediated immune protection (Sherritt et al., 2001). Minev and her colleagues demonstrated that linking signal peptide to a defined MHC-class I-restricted epitope, as in the case of the Melanoma MART-1 TAA, enhances the epitope presentation i.e. the signal peptide enhances the ability of the epitope to attract and activate CD8+ T cells (Minev B R, et al, 2000). In both of these reports, immunity to the TAA epitopes was increased in both Transporter for Antigen Presentation (TAP)-deficient and TAP-expressing cells, suggesting that signal peptides can facilities TAP independent presentation of TAA epitopes.

According to these reports the signal peptide merely acts as a chaperon or tag for selected epitopes/Vaccines. These vaccines, however, suffer from several drawbacks as they utilize selected immunogenic epitopes, MHC-class I-restricted peptides with limited repertoire for activation, or non-defined immunogenic epitopes with non-specific activity.

The MUC1 TAA and its Role in Cancer

MUC1 is one of the most promising TAAs known today. This polymorphic epithelial mucin, encoded by the MUC1 gene, is a high-molecular-weight glycoprotein with few alternative-splicing variants encoding for both a transmembranal (i.e. across the cell membrane) and a secreted (i.e. circulating) product both expressed in a broad range of tumors (Graham et al., 1996; Ho et al., 1993). MUC1 is one of the few known targets that are expressed by more than 90 percent of common solid tumor cancers including Colon, Gastric, Lung, Renal Cell (RC), Transitional Cell (TC), Prostate, Pancreas, Breast, Ovary and Thyroid. It is also associated with many non-solid tumors among which: Lymphoma, Leukemia, and Multiple Myeloma (MM). The association of MUC1 with cancer progression was well documented in the literature (McGuckin et al., 1995). Many groups have shown that MUC1 is expressed on the cell surface of most MM cell lines, MM patient plasma cells and circulating B cells, and plasmacytomas (Treon S P et al., 2000). In addition, soluble MUC1 has also been detected in peripheral blood plasma of MM patients by the use of a noncommercial enzyme-linked immunosorbent assay (ELISA). Treon and his colleagues also determined elevation in soluble MUC1 levels in MM patients using an immunoassay that recognizes the CA27.29 MUC1 epitope. He further demonstrate that MUC1 levels are elevated in both bone marrow (BM) and peripheral blood plasma of MM patients in comparison to healthy donors, and that BM MUC1 levels are associated with tumor burden in MM patients.

A major feature of the MUC1 molecule (in both the transmembranal and the secreted variants) is the presence of a highly immunogenic extracellular tandem repeat array (TRA) heavily O-glycosylated at serine and threonine residues. It was shown that this extracellular TRA domain can be recognized by monoclonal antibodies (MAbs), as well as MHC-restricted CD8+ T cells (CTLs) such as HLA-A11 and HLA-A2.1-CTLs. In spite of the high immunogenicity of the TRA, its role as a potential target/vaccine is ambiguous. One of the major drawbacks for targeting MUC1's TRA stems from the finding that most of the immunogenic epitope in the TRA domain exists both in the extracellular as well as in the secreted products. That is to say, that the secreted variant is acting as decoy that negatively interferes or competes with any potential drugs/vaccines. In addition, reports have indicated that synthetic peptides derived from MUC1's TRA cause suppression of human T-cell proliferative responses (Fung and Longenecker, 1991).

More recently, reports have showed Class I (HLA-A2.1-restricted) CD8+ T cell epitopes which were deduced from other domains on the MUC1 protein (Carmon et al., 2000, Brossart et al., 1999; WO 00/06723; WO 00/63363). These epitopes (termed D6 or VXL1 and M1.2 or VXL2) were shown to be restricted only to a single class I epitope.

Another example of a tumor associated antigen is BAGE. BAGE, codes for a putative protein of 43 amino acids and seems to belong to a family of several genes. Gene BAGE is expressed in 22% of melanomas, 30% of infiltrating bladder carcinomas, 10% of mammary carcinomas, 8% of head and neck squamous cell carcinomas, and 6% of non-small cell lung carcinomas. It is silent in normal tissues with the exception of testis (Boel et al., 1995).

Another example, Arginine rich, mutated in early stage of tumors (ARMET), also designated Arginine-rich protein (ARP), is a highly conserved gene that maps to human chromosomal band 3p21.1. This gene contains an imperfect trinucleotide repeat which encodes a string of arginines. A specific mutation (ATG50→AGG) was detected within this region of the gene in a high percentage of sporadic renal cell carcinomas, squamous cell carcinomas of the head and neck, small cell lung cancer cell lines, non-small cell lung carcinomas, breast tumors, and prostate tumors (Shridhar et al., 1996).

SUMMARY OF THE INVENTION

The present invention relates to promiscuous peptide vaccines comprising multiple MHC class I, and MHC class II epitopes of a given protein antigen. More particularly, the present invention relates to promiscuous peptide vaccines comprising multiple MHC class I and MHC class II epitopes with the specificity of a given antigen derived from the entire signal peptide domain of that protein antigen. These MHC class I and MHC class II epitopes have a high frequency in the population and thus the vaccine is effective in a large portion of the population.

The present invention thus provides a peptide vaccine which is able to induce strong, comprehensive response in the majority of the target population against said antigen. More specifically, but without wishing to be limited to a single hypothesis, such a vaccine preferably combines activation of both CD4+ and CD8+ T cells via multiple CD4+ and CD8+-restricted epitopes which are present within the internal sequences of the vaccine and are derived from the same antigen.

In one aspect, the present invention relates to such peptide vaccines comprising the signal peptide domain of tumor associated antigens (TAA) or the signal peptide domain of proteins which are over-expressed in tumor cells.

In one embodiment, the present invention relates to peptide vaccines comprising the signal peptide of a protein which is either a TAA or is over-expressed in tumor cells, wherein said peptides are recognized and presented by more than 50% of the MHC class I and MHC Class II alleles in the population. Preferably, said peptide is not longer than 50 amino acids, more preferably, not longer than 25 amino acids.

In one embodiment the peptide vaccines of the invention comprise the signal peptide of proteins selected from the group consisting of Armet, HSP60, CANX, MTHFD2, FAP, MMP6, BAGE-1, GNTV, Q5H943, MUC1, CEA, Pmel, Kallikrein-4, Mammaglobin-1, MART-1, GPR143-OA1, PSA, TRP1, Tyrosinase, FGF-5, NEU proto-oncogene, Aft, MMP-2, PSMA, Telomerase-associated protein 2, PAP, Uroplakin II and Proteinase 3, i.e. SEQ ID Nos. 1-28, respectively (Table 1).

According to one specific embodiment, the present invention relates to tumor associated antigen peptides comprising the signal peptide domain of the polymorphic epithelial mucin, encoded by the MUC1 gene.

The present invention thus provides a promiscuous peptide vaccine comprising the MUC1 signal peptide domain which is able to induce strong, comprehensive response in the majority of the target population against any MUC1 positive tumor.

The MUC1 signal peptide-derived peptide vaccines are able to bind to the majority of MHC Class I alleles in the population and thus induce CD8+ T-cell mediated cell lysis, and are also able to bind to bind to the majority of MHC Class II alleles in the population and thus prime an effective CD4+ T-cell mediated immune response.

In one embodiment the MUC1 signal peptide-derived peptide vaccine comprises the amino acid sequence MTPGTQSPFFLLLLLTVLTVV (SEQ ID NO. 10).

In another embodiment, the peptide vaccine of the invention comprises a mixture of at least two short peptides of preferably about nine amino acid residues in length derived from the signal peptide domain of the MUC1 protein. These peptides represent various MHC Class I and Class II epitopes which are included in the MUC1 signal peptide. Their combination results in effective binding of the vaccine composition to various alleles of MHC class I and MHC class II molecules, and thus to the induction of an immune response to tumors expressing the MUC1 protein. This response may include inducing "help" for priming a strong T cell activity via CD4+ T cell activation, combined with induction of CD8+ T cell activation, and potent cellular activity (CTL) against MUC1 expressing tumors.

Specifically, the mixture of short peptides comprises at least two peptides selected from the group consisting of SEQ ID NO: 29-39.

In one embodiment the mixture of short peptides comprises VXL01 (SEQ ID NO 29), VXL02 (SEQ ID NO 30), VXL04 (SEQ ID NO 31) and VXL05 (SEQ ID NO 32).

In another specific embodiment, the present invention relates to peptide vaccines derived from the signal peptide domain of the BAGE-1 gene.

In one embodiment the BAGE-1 signal peptide-derived peptide vaccine comprises the amino acid sequence MAARAVFLAL SAQLLQA (SEQ ID NO. 7).

In another specific embodiment, the present invention relates to peptide vaccines derived from the signal peptide domain of the Armet gene.

In one embodiment the Armet signal peptide-derived peptide vaccine comprises the amino acid sequence MWATQGLAVA LALSVLPGSR A (SEQ ID NO. 1).

The present invention also concerns use of the peptide vaccines described above in the preparation of pharmaceutical compositions for treating or inhibiting cancer.

The invention further concerns pharmaceutical compositions comprising said peptide vaccines and the use of said peptide vaccines or said pharmaceutical compositions as anti-tumor vaccines to treat or inhibit the development of cancer. Specifically, for the treatment of tumors which over-expresses the protein from which the signal peptide vaccine was derived, for example, MUC1-expressing cancer, BAGE-1-expressing cancer, or Armet-expressing cancer.

The invention further concerns nucleic acid molecules encoding said peptides, and antigen presenting cells (APC), e.g. dendritic cells, presenting said peptides, as well as pharmaceutical compositions comprising said nucleic acid molecules, or said cells.

The invention also concerns use of the peptide vaccines for enrichment of T cell populations in vitro. Thus obtaining a peptide-specific enriched T cell population.

The invention further concerns the use of said nucleic acid molecules, cells, or pharmaceutical compositions comprising same as anti-tumor vaccines to treat or inhibit the development of cancer. Specifically, for the treatment of tumors which over-expresses the protein from which the signal peptide vaccine was derived, for example, MUC1-expressing cancer, BAGE-1-expressing cancer, or Armet-expressing cancer.

Further aspects of the present invention are directed to a method for treating or for inhibiting the development of cancer by administering the pharmaceutical compositions of the present invention to a patient in need thereof.

The pharmaceutical compositions of the invention may be adapted for use in combination with other anti neoplastic agents.

TABLE 1

List of signal peptide vaccines

| SEQ ID | Protein | SP Prediction NN | HMM | SP Length | SP SEQUENCE | MHC-I | MHC-II (Genotypes) | MHC-II (Serotypes) |
|---|---|---|---|---|---|---|---|---|
| 1 | Armet | 0.87 | 1 | 21 | MWATQGLAVA LALSVLPGSR A | 66 | 16 | 47 |
| 2 | HSP60 | 0.31 | 0.19 | 26 | MLRLPTVFRQ MRPVSRVLAP HLTRAYA | 84 | 45 | 72 |
| 3 | CANX | 0.91 | 0.99 | 20 | MEGKWLLCML LVLGTAIVEA | 81 | 52 | 52 |
| 4 | MTHFD2 | 0.43 | 0.99 | 20-35 (P/G) | MAATSLMSAL AARLLQPAHS CSLRLRPFHL AAVRN | 76 | 41 | 64 |
| 5 | FAP | 0.57 | 0.36 | 23 | MKTWVKIVFG VATSAVLALL VMCI | 69 | 48 | 67 |
| 6 | MMP9 | 0.92 | 1 | 19 | MSLWQPLVLV LLVLGCCFA | 72 | 52 | 47 |
| 7 | BAGE-1 | 0.77 | 1 | 17 | MAARAVFLAL SAQLLQA | 78 | 16 | 45 |
| 8 | GNTV | 0.56 | 0.34 | 26 | MALFTPWKLS SQKLGFFLVT FGFIWG | 85 | 36 | 65 |
| 9 | Q5H943 | 0.56 | 0.32 | 19 | MNFYLLLASS ILCALIVFW | 75 | 45 | 44 |
| 10 | MUC1 | 0.8 | 1 | 21 | MTPGTQSPFF LLLLLTVLTVV | 83 | 52 | 60 |
| 11 | CEA | 0.7 | 0.99 | 34 | MESPSAPPHR WCIPWQRLLL TASLLTFWNP PTTA | 81 | 45 | 70 |
| 12 | Pmel | 0.78 | 0.93 | 23 | MDLVLKRCLL HLAVIGALLA VGA | 82 | 36 | 52 |
| 13 | Kallikrein-4 | 0.71 | 0.98 | 26 | MATAGNPWGW FLGYLILGVA GSLVSG | 85 | 52 | 56 |
| 14 | Mammaglobin-1 | 0.86 | 1 | 18 | MKLLMVLMLA ALSQHCYA | 79 | 52 | 61 |
| 15 | MART-1 | No | 0.99 | 27-50 | MPREDAHFIY GYPKKGHGHS YTTAEEAAGI GILTVILGVL LLIGCWYCRR | 87 | 38 | 74 |
| 16 | GPR143-OA1 | 0.43 | 0.32 | 44 | MASPRLGTFC CPTRDAATQL VLSFQPRAFH ALCLGSGGLR LALGLLOL | 87 | 22 | 74 |
| 17 | PSA | 0.81 | 1 | 17 | MWVPVVFLTL SVTWIGA | 71 | 45 | 58 |
| 18 | TRP1 | 0.84 | 1 | 24 | MSAPKLLSLG CIFFPLLLFQ QARA | 80 | 32 | 49 |
| 19 | Tyrosinase | 0.84 | 1 | 17 | MLLAVLYCLL WSFQTSA | 71 | 38 | 51 |
| 20 | FGF-5 | 0.89 | 1 | 20 | MSLSFLLLLF FSHLILS | 78 | 48 | 59 |
| 21 | NEU proto-oncogene | 0.9 | 1 | 22 | MELAALCRWG LLLLALLPPGA AS | 88 | 32 | 52 |
| 22 | Aft | 0.82 | 0.98 | 18 | MKWVESIFLI FLLNFTES | 81 | 47 | 69 |
| 23 | MMP-2 | 0.79 | 1 | 29 | MEALMARGAL TGPLRALCLL GCLLSHAAA | 84 | 36 | 41 |

TABLE 1-continued

List of signal peptide vaccines

| SEQ ID | Protein | SP Prediction NN | SP Prediction HMM | SP Length | SP SEQUENCE | MHC-I | MHC-II (Genotypes) | MHC-II (Serotypes) |
|---|---|---|---|---|---|---|---|---|
| 24 | PSMA | 0.42 | 0.01/0.99 (sp/sp+ anchor) | 40 | MWNLLHETDS AVATARRPRW LCAGALVLAG GFFLLGFLFG | 86 | 34 | 77 |
| 25 | Telomerase-assoc. protein 2 | 0.2 | 0.16 | 23 | MPRAPRCRAV RSLLRSHYRE VLP | 69 | 47 | 77 |
| 26 | PAP | 0.56 | 0.66 | 27 | MFDKTRLPYV ALDVLCVLLA GLPFAIL | 84 | 52 | 72 |

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF THE INVENTION

Figure 1:
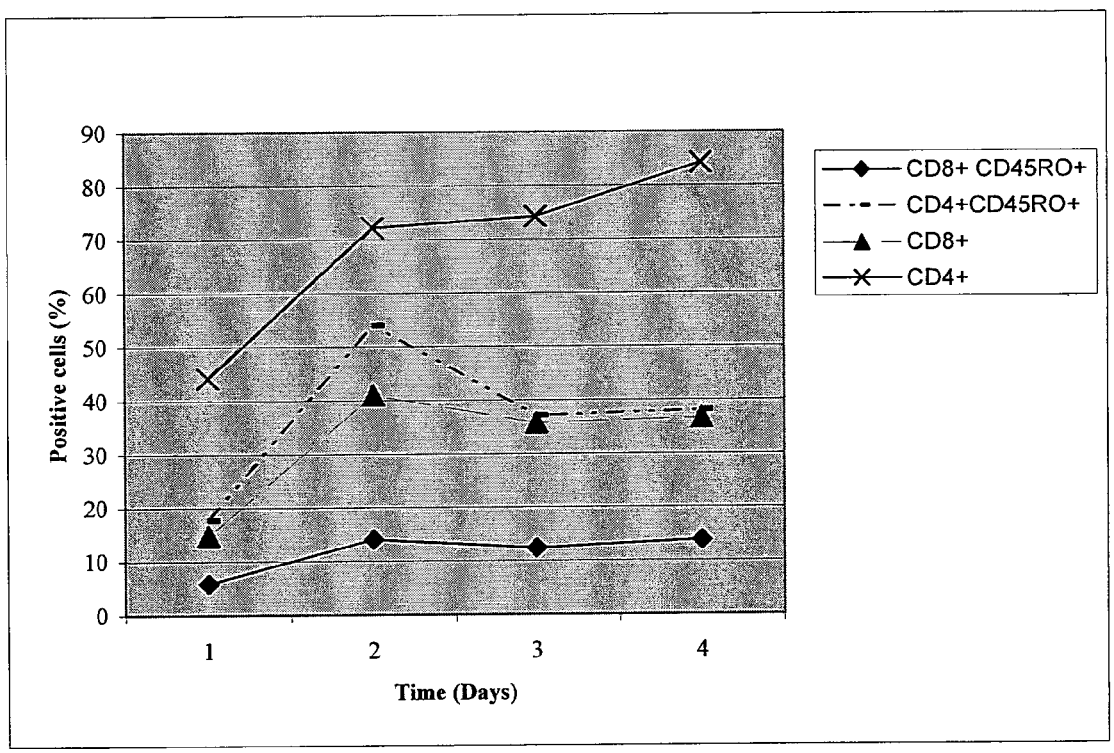
FIG. 1 is a graph showing results of an ELISA quantitative assay measuring cytokine secretion profiles of a specific T cell subpopulation developed via repeated stimulation with ImMucin. The results represent one out of two experiments using four different donors.

The present invention provides antigen specific vaccines which are capable of inducing a robust T-cell immunity and which are applicable to the majority of the population.

Whilst signal peptides (SP) have been used as non-specific immune stimulators for elevating the immunity of antigenic epitopes to which they were linked, their use as a source for antigens/epitopes with independent immunogenic properties, in addition to their stimulatory properties was not disclosed previously.

The present invention is based on the surprising finding that SP-derived vaccines are able to bind simultaneously to multiple alleles of both MHC class I and MHC class II i.e. $CD4^+$ and $CD8^+$-restricted epitopes. A signal peptide vaccine, although containing just one sequence, could thus be compared to a large number of single Class I and Class II epitopes, used in a mixture. This newly discovered feature of SP-vaccines facilitates the generation of a robust immune response in the majority of the target population. Moreover, but without wishing to be bound by theory, it should be emphasized that signal peptide-based vaccines bare the ability to independently penetrate the ER and thus, at least partially, avoid immune escape mechanisms such as TAP deficiency.

One non-limiting procedure/algorithm for selecting candidate vaccines in accordance with the present invention is described below. This procedure combines in-silico analysis and reverse immunology.

Specifically, the objective of the predictive algorithm is to identify and obtain signal peptide (SP) targets with a potential role as cancer vaccines. The putative targets should have the following characteristics:

Differentially expressed in tumor cells;
Eligible targets for an immune assault; and
Predicted as binding MHC Class I and Class II alleles (and therefore likely to be immunogenic) in the majority of the population.

Providing a List of Putative Cancer Protein Targets

A person versed in the art may find many information sources in the literature, providing data on tumor associated proteins. As a non-limiting example, see Rhodes D R and Chinnaiyan A M. (2005), who performed a meta-analysis of many microarray gene expression studies, checking differential gene expression in normal vs. cancer tissues of the most prominently appearing cancers. In addition, many web available databases provide lists of tumor-specific antigens. Non-limiting examples include:

a. Tumor specific (unique) antigens
b. Tumor antigens that are tissue-specific (differentiation) antigens
c. Tumor antigens that are overexpressed in cancer cells vs. the respective normal tissue Exclusion of Non Eligible Targets for an Immune Assault Proteins with the following attributes are removed from the list of putative targets as being non eligible for an immune assault:

Proteins that are located sub-cellularly, e.g. in organelles or in any other location that does not require transport from the ER-Golgi, and thus have no signal peptides (e.g. purely cytoplasmic proteins, such as ATP-citrate synthase).

Proteins which function in basic or homeostatic functions in all cells (e.g. purine synthesis, for example phosphoribosylaminoimidazole carboxylase, phosphoribosylaminoimidazole succinocarboxamide synthetase (PAICS), succinate dehydrogenase, cytochrome b556 subunit (SDHC), cell division cycle 2 (CDC2).

Proteins that are ubiquitously expressed in many tissues (e.g. tubulin, beta TUBB, RNA binding motif protein 4 (RBM4).

Immune-related proteins (e.g. proteasome (prosome, macropain) activator subunit 2 PSME2, CD213a2, Macrophage colony-stimulating factor (M-CSF).

Identifying Signal Peptide Sequences

Proteins that are found to be eligible targets for an immune assault are next examined for the presence of a signal peptide. This may be done by using appropriate computer software, e.g. the Signal P 3.0. The Signal P 3.0 program uses both a neural network (NN) algorithm and a Hidden Markov models (HMM) algorithm for selection of the signal. A sequence was considered to be a signal peptide whenever a score of over 0.2 was received in one or more of the algorithms. Sequences having a score of above 0.7 are preferred. Sequences having a score of above 0.8 are most preferred.

Preferably, cancer protein targets, eligible for an immune assault and having an identified signal peptide sequence of 17-50 amino acids are selected for further examination of predicted binding to MHC alleles.

Predicting MHC Class I and II Binding

A prediction of putative binding of the selected candidate signal peptide sequences to frequently occurring HLA haplotypes is made based on information concerning HLA allele frequency (class I and II) which may be obtained, for example, from the dbMHC site belonging to the NCBI.

Alleles of HLA class I (HLA-A, B, C) and HLA class II (HLA-DRB1) which most frequently appear in the population are listed in Table 2. The table specifies the most frequent alleles (appearing in over 5% of the population) for which prediction methods exist.

TABLE 2

Alleles of HLA class I (HLA-A, B, C) and HLA class II (HLA-DRB1) which most frequently appear in the population

| Class I Alleles | | Class II Alleles (Genotype) | | Class II Alleles (Serotypes) | |
|---|---|---|---|---|---|
| Allele | Frequency | Allele | Frequency | Allele | Frequency |
| HLA-A24 | 0.36 | DR-B1 1501 | 0.13 | DR-B1 04 | 0.31 |
| HLA-A0201 | 0.27 | DR-B1 0301 | 0.13 | DR-B1 15 | 0.24 |
| HLA-A1101 | 0.2 | DR-B1 1101 | 0.13 | DR-B1 11 | 0.17 |
| HLA-A01 | 0.12 | DR-B1 0701 | 0.13 | DR-B1 08 | 0.16 |
| HLA-A03 | 0.1 | DR-B1 0401 | 0.07 | DR-B1 03 | 0.16 |
| HLA-A3101 | 0.07 | DR-B1 1302 | 0.07 | DR-B1 13 | 0.15 |
| HLA-A6801 | 0.05 | DR-B1 0901 | 0.03 | DR-B1 07 | 0.13 |
| HLA-B40 | 0.24 | | | DR-B1 01 | 0.09 |
| HLA-B07 | 0.11 | | | DR-B1 09 | 0.06 |
| HLA-B3501 | 0.09 | | | | |
| HLA-B5101 | 0.09 | | | | |
| HLA-B08 | 0.08 | | | | |
| HLA-B5801 | 0.07 | | | | |
| HLA-B4403 | 0.06 | | | | |
| HLA-Cw0702 | 0.26 | | | | |
| HLA-Cw0401 | 0.21 | | | | |
| HLA-Cw0602 | 0.13 | | | | |

Subsequently, the binding strength of the previously identified signal peptides to the HLA alleles is predicted using any of numerous available software programs. The following is a non-limiting list of available prediction programs:

BIMAS may be used for the prediction of HLA class I alleles.
Propred may be used to predict most DRB1 genotypes.
Immune Epitope
may be used for the prediction of the HLA-RB 1-0901 genotype that is not predicted by Propred.
MHC2Pred may be used to predict various DRB1 serotypes.

Defining Differential Strength of Binding

In each of the programs used, various differential strength of binding are defined:
BIMAS: Strong=peptide score of 100+, Medium=10-100, Weak=5-10.
Propred: Strong=top 1% of binders, Medium=1-2% of binders, Weak=2-3% of binders.
Immune Epitope: Strong=$IC_{50}$ of 0.01 nM-10 nM, Medium=10-100 nM, Weak=100-10,000 nM.
MHC2Pred: Strong=cutoff 1.0, medium=cutoff 0.5, Weak=cutoff 0. As serotype prediction is expected to be less accurate than genotype prediction, only high and medium binders were predicted with MHC2Pred.

Determining the Predicted Percentage of Population that has Alleles Having Predicted Binding Peptides within a Specific Signal Peptide To calculate the probability that a patient (or a population) has one or more alleles predicted to bind a certain signal peptide, a statistic calculation using complementary probabilities is performed. Independent distribution of alleles in the population was assumed.

Explanatory calculation: if peptide X was predicted as a peptide that binds to only four HLA-class I alleles: HLA-A1 (frequency 0.1), HLA-B2 (freq=0.2), HLA-B3 (freq.=0.3), and HLA-C4 (freq. 0.4) then the probability that it would bind neither of these alleles is the product of the probabilities that it would bind neither HLA-A1 (1-0.1), nor HLA-B2 (1-0.2), nor HLA-B3 (1-0.3), nor HLA-C4 (1-0.4) therefore the probability is:

$(1-0.1)(1-0.2)(1-0.3)(1-0.4)=0.3024$.

The probability that the patient has one or more of the binding alleles is 1 minus the probability that he would have none of the binding alleles:
$1-0.3024=0.6976$ The calculation was done separately for the HLA class I alleles, the HLA-class II alleles (genotypes), and the HLA class II alleles (serotypes). Each list contained no overlapping alleles (e.g. HLA-A02 and HLA-A0201).

Peptides that would bind in the majority (>50%) of the population (both in the HLA class I and in the HLA class II alleles) were further followed. In addition, targets that have an abundance of at least 40% in their class II serotypes were also included. This is due to the fact that only about 75% of class II serotypes were covered in the screen, assuming that with inclusion of the remaining 25%, the threshold of 50% will be achieved.

Selecting Appropriate Vaccine Candidates

Preferably, the most suitable SP vaccine candidates are chosen according to the following criteria:
1. Having a high score for SP of more than 0.7 in the Signal P software, as measured by at least one but preferably by both tests, NN and HMM. Having a higher score than 0.8 in the Signal P software is preferred.
2. >50% allele frequency for both Class I, and Class II molecules.
3. Length of SP Peptide of up to 50 AA, preferably up to 30 AA, most preferably up to 25 AA.
4. Known role as a tumor associate antigen (TAA) or being over expressed in tumor vs. normal tissues.
5. Broad Expression of the TAA in various cancer tissues.

Utilizing this novel procedure, the entire sequence of signal peptide domains from over 30 potential targets, predominantly TAA was scanned in order to identify vaccines having both immune enhancing and immunogenic properties. Preferred candidates conforming to the above-defined criteria were identified and are listed in Table 1.

In one specific example, a MUC1 SP vaccine (hereinafter termed "VXL100" or "ImMucin") was prepared. The ImMucin vaccine of the invention is composed of a 21 amino acid (AA)-long peptide derived from the signal peptide domain of the MUC1 protein and comprises the amino acid sequence MTPGTQSPFFLLLLLTVLTVV (SEQ ID NO 10).

This peptide vaccine is processed in the antigen-presenting cell (APC) and presented to immune effector cells by MHC class I, and II molecules.

ImMucin harbors a set of unique characteristics as listed below:

ImMucin targets the mucin MUC1 expressed on the surface of Multiple Myeloma and other solid and non-solid cancers.

Unlike other MUC1 vaccines which focus on the entire protein, ImMucin does not contain any non-specific epitopes that could dilute and disturb specific anticancer immunity.

ImMucin was selected due to its ability to bind multiple MHC Class I and Class II alleles. This would potentially offer:

A broad activation of multiple T cell clones both CD8+ and CD4+ T cells, by use of a single 21 AA peptide. This could actually be considered equal to a selected mixture of 11 different immunogenic epitopes.

A positive respond is expected in the majority of the target patients i.e. covering most of the allelic repertoire among the Caucasian and other populations.

Due to the unique sequence of Signal peptides, ImMucin has superior immunogenicity which may, at least partially, circumvent immune escape mechanisms such as TAP-deficiency of cancer cells.

According to one embodiment, the present invention concerns a vaccine comprising a mixture of short peptides comprising MHC Class I and II epitopes within the MUC1 signal domain. These short peptides include:

```
SEQ ID NO 29:   LLLTVLTVV  (designated VXL01)

SEQ ID NO 30:   LLLLTVLTV  (designated VXL02)

SEQ ID NO 31:   TQSPFFLLL  (designated VXL04)

SEQ ID NO 32:   SPFFLLLLL  (designated VXL05)

SEQ ID NO 33:   FLLLLLTVL

SEQ ID NO 34:   LLLLLTVLT

SEQ ID NO 35:   GTQSPFFLL

SEQ ID NO 36:   TPGTQSPFF

SEQ ID NO 37:   FFLLLLLTV

SEQ ID NO 38:   MTPGTQSPF

SEQ ID NO 39:   QSPFFLLLL
```

As used herein, the term "tumor associated antigen" or "TAA" refers to antigens or proteins that are highly correlated with certain tumor cells. They are not usually expressed in normal cells, or are expressed at a higher extent in tumor cells than in normal cells.

The nomenclature used to describe peptide and/or polynucleotide compounds of the invention follows the conventional practice wherein the amino group (N-terminus) and/or the 5' are presented to the left and the carboxyl group (C-terminus) and/or 3' to the right.

As used herein, the term "peptide" refers to a molecular chain of amino acids, which, if required, can be modified in vivo or in vitro, for example by manosylation, glycosylation, amidation (specifically C-terminal amides), carboxylation or phosphorylation with the stipulation that these modifications must preserve the biological activity of the original molecule. In addition, peptides can be part of a chimeric protein.

Functional derivatives of the peptides are also included in the present invention. Functional derivatives are meant to include peptides which differ in one or more amino acids in the overall sequence, which have deletions, substitutions, inversions or additions. Amino acid substitutions which can be expected not to essentially alter biological and immunological activities have been described. Amino acid replacements between related amino acids or replacements which have occurred frequently in evolution are, inter alia Ser/Ala, Ser/Gly, Asp/Gly, Asp/Asn, Ile/Val see Dayhof M. D (1978). Based on this information, Lipman and Pearson (1985) developed a method for rapid and sensitive protein comparison and determining the functional similarity between homologous polypeptides.

The peptides according to the invention can be produced synthetically, by recombinant DNA technology. Methods for producing synthetic peptides are well known in the art.

The organic chemical methods for peptide synthesis are considered to include the coupling of the required amino acids by means of a condensation reaction, either in homogenous phase or with the aid of a so-called solid phase. The condensation reaction can be carried out as follows:

Condensation of a compound (amino acid, peptide) with a free carboxyl group and protected other reactive groups with a compound (amino acid, peptide) with a free amino group and protected other reactive groups, in the presence of a condensation agent;

Condensation of a compound (amino acid, peptide) with an activated carboxyl group and free or protected other reaction groups with a compound (amino acid, peptide) with a free amino group and free or protected other reactive groups.

Activation of the carboxyl group can take place, inter alia, by converting the carboxyl group to an acid halide, azide, anhydride, imidazolide or an activated ester, such as the N-hydroxy-succinimide, N-hydroxy-benzotriazole or p-nitrophenyl ester.

The most common methods for the above condensation reactions are: the carbodiimide method, the azide method, the mixed anhydride method and the method using activated esters, such as described in The Peptides, Analysis, Synthesis, Biology Vol. 1-3 (Ed. Gross, E. and Meienhofer, J.) 1979, 1980, 1981 (Academic Press, Inc.).

Production of peptides by recombinant DNA techniques is a general method which is known, but which has a lot of possibilities all leading to somewhat different results. The polypeptide to be expressed is coded for by a nucleic acid sequence.

Also part of the invention is the nucleic acid sequence comprising the sequence encoding the peptides according to the present invention.

As is well known in the art, the degeneracy of the genetic code permits substitution of bases in a codon to result in another codon still coding for the same amino acid, e.g., the codon for the amino acid glutamic acid is both GAT and GAA. Consequently, it is clear that for the expression of a polypeptide with an amino acid sequence as shown in any of SEQ ID NO: 1-28 use can be made of a derivate nucleic acid sequence with such an alternative codon composition thereby different nucleic acid sequences can be used.

"Nucleotide sequence" as used herein refers to a polymeric form of nucleotides of any length, both to ribonucleic acid (RNA) sequences and to deoxyribonucleic acid (DNA) sequences. In principle, this term refers to the primary structure of the molecule. Thus, this term includes double and single stranded DNA, as well as double and single stranded RNA, and modifications thereof.

The nucleotide sequences encoding the peptide vaccines of the invention can be used for the production of the peptides using recombinant DNA techniques. For this, the nucleotide sequence must be comprised in a cloning vehicle which can be used to transform or transfect a suitable host cell.

A wide variety of host cell and cloning vehicle combinations may be usefully employed in cloning the nucleic acid sequence. For example, useful cloning vehicles may include chromosomal, non-chromosomal and synthetic DNA sequences such as various known bacterial plasmids, and wider host range plasmids such as pBR 322, the various pUC, pGEM and pBluescript plasmids, bacteriophages, e.g. lambda-gt-Wes, Charon 28 and the M13 derived phages and vectors derived from combinations of plasmids and phage or virus DNA, such as SV40, adenovirus or polyoma virus DNA.

Useful hosts may include bacterial hosts, yeasts and other fungi, plant or animal hosts, such as Chinese Hamster Ovary (CHO) cells, melanoma cells, dendritic cells, monkey cells and other hosts.

Vehicles for use in expression of the peptides may further comprise control sequences operably linked to the nucleic acid sequence coding for the peptide. Such control sequences generally comprise a promoter sequence and sequences which regulate and/or enhance expression levels. Furthermore, an origin of replication and/or a dominant selection marker are often present in such vehicles. Of course, control and other sequences can vary depending on the host cell selected.

Techniques for transforming or transfecting host cells are quite known in the art (for instance, Maniatis et al., 1982/1989, Molecular cloning: A laboratory Manual, Cold Spring Harbor Lab.).

The present invention also provides a polynucleotide encoding the signal peptide vaccine of the invention as part of a pharmaceutical composition preferably for targeted treatment of a tumor.

Further aspects of the present invention are directed to a method for treating or for inhibiting the development of cancer by administering the pharmaceutical compositions of the present invention to a patient in need thereof.

The present invention describes a method for treating or inhibiting the development of solid tumors for example, Colon, Gastric, Lung, Renal Cell (RC), Transitional Cell (TC), Prostate, Pancreas, Breast, Ovary or Thyroid cancers, as well as non-solid tumors such as Lymphoma, Leukemia, and Multiple Myeloma.

Specifically, the present invention provides a method for treating or for inhibiting the development of MUC1-expressing cancers by administering the MUC1 signal peptide-derived peptide vaccine of the present invention to a patient in need thereof.

In another embodiment the present invention provides a method for treating or for inhibiting the development of BAGE1-expressing cancers by administering the BAGE1 signal peptide-derived peptide vaccine of the present invention to a patient in need thereof. Such cancers include melanoma, bladder carcinoma, mammary carcinoma, head and neck squamous cell carcinoma, and non-small cell lung carcinomas.

In another embodiment the present provides a method for treating or for inhibiting the development of Armet-expressing cancers by administering the Armet signal peptide-derived peptide vaccine of the present invention to a patient in need thereof. Such cancers include renal cell carcinomas, lung, breast, prostate, squamous cell carcinoma, head and neck carcinoma, pancreatic carcinoma.

The peptide vaccine of the invention is administered in an immunogenically effective amount with or without a co-stimulatory molecule. According to the method of the invention, the peptide vaccine may be administrated to a subject in need of such treatment for a time and under condition sufficient to prevent, and/or ameliorate the condition of cancer being treated.

The antigen and co-stimulatory molecule, if used, are formulated, separately or as a "chimeric vaccine" formulation, with a pharmaceutically acceptable carrier and administered in an amount sufficient to elicit a T lymphocyte-mediated immune response.

According to the methods of the invention, the peptide may be administered to subjects by a variety of administration modes, including by intradermal, intramuscular, subcutaneous, intravenous, intra-atrial, intra-articular, intraperitoneal, parenteral, oral, rectal, intranasal, intrapulmonary, and transdermal delivery, or topically to the eyes, ears, skin or mucous membranes. Alternatively, the antigen may be administered ex-vivo by direct exposure to cells, tissues or organs originating from a subject (Autologus) or other subject (Allogeneic), optionally in a biologically suitable, liquid or solid carrier.

In certain embodiments of the invention, the peptides or pharmaceutical composition with or without a co-stimulatory molecule are delivered to a common or adjacent target site in the subject, for example to a specific target tissue or cell population in which the vaccine formulation is intended to elicit an immune response. Typically, when the peptide or pharmaceutical composition and the optional co-stimulatory molecule are administered separately, they are delivered to the same or closely proximate site(s), for example to a single target tissue or to adjacent sites that are structurally or fluidly connected with one another (e.g., to allow direct exposure of the same cells, e.g., fluid flow transfer, dissipation or diffusion through a fluid or extracellular matrix of both vaccine agents). Thus, a shared target site for delivery of antigen and co-stimulatory molecule can be a common surface (e.g., a mucosal, basal or lunenal surface) of a particular target tissue or cell population, or an extracellular space, lumen, cavity, or structure that borders, surrounds or infiltrates the target tissue or cell population.

For prophylactic and treatment purposes, the peptide antigen with or without a co-stimulatory molecule may be administered to the subject separately or together, in a single bolus delivery, via continuous delivery (e.g., continuous intravenous or transdermal delivery) over an extended time period, or in a repeated administration protocol (e.g., on an hourly, daily or weekly basis). The various dosages and delivery protocols contemplated for administration of peptide and co-stimulatory molecule, in simultaneous or sequential combination, are immunogenically effective to inhibit the occurrence or alleviate one or more symptoms of the target cancer in the subject. An "immunogenically effective amount" of the antigen thus refers to an amount that is, in combination, effective, at dosages and for periods of time necessary, to elicit a specific T lymphocyte mediated immune response. This response can be determined by conventional assays for T-cell activation, including but not limited to assays to detect proliferation, specific cytokine activation and/or cytolytic activity.

In more detailed aspects of the invention, the amount of peptide vaccine is immunogenically effective to achieve a desired cancer inhibitory effect in the subject. In specific embodiments, an immunogenically effective amount of the peptide, depending on the selected mode, frequency and duration of administration, will effectively prevent cancer, or will inhibit progression of a cancerous condition in the subject. Alternatively or in addition to these effects, an immunogenically effective dosage of the antigen, which may include repeated doses within an ongoing prophylaxis or treatment regimen, will alleviate one or more symptoms or detectable conditions associated with a cancerous disorder. This includes any detectable symptom or condition amenable to prophylaxis and/or treatment with the vaccines of the invention, for example symptoms or conditions associated with breast cancer, cervical cancer, prostate cancer, colon cancer, melanoma and other cancerous conditions.

For prophylactic and therapeutic use, peptide antigens might be formulated with a "pharmaceutical acceptable carrier". As used herein, "pharmaceutically acceptable carrier" includes any and all solvents, dispersion media, coatings, antibacterial and antifungal agents, isotonic and absorption enhancing or delaying agents, and other excipients or additives that are physiologically compatible. In specific embodiments, the carrier is suitable for intranasal, intravenous, intramuscular, intradermal, subcutaneous, parenteral, oral, transmucosal or transdermal administration. Depending on the route of administration, the active compound may be coated in a material to protect the compound from the action of acids and other natural conditions which may inactivate the compound.

Peptide vaccine may be administered to the subject in the form of a peptide solution per se or a combination of a peptide with an appropriate auxiliary agent using an injector. Alternatively, the peptide vaccine may be percutaneously administered through mucous membrane by, for instance, spraying the solution. The unit dose of the peptide typically ranges from about 0.01 mg to 100 mg, more typically between about 100 micrograms to about 5 mg, which may be administered, one time or repeatedly, to a patient.

Examples of auxiliary agents which can be formulated with or conjugated to peptide or protein antigens and/or vectors for expressing co-stimulatory molecules to enhance their immunogenicity for use within the invention include cytokines (e.g. GM-CSF), bacterial cell components such as BCG bacterial cell components, immunostimulating complex (ISCOM), extracted from the tree bark called QuillA (Morein et al., 1984 incorporated herein by reference), QS-21, a saponin-type auxiliary agent (Wu et al., (1992), incorporated herein by reference), Montanide ISA 51VG, liposomes, aluminum hydroxide (alum), bovine serum albumin (BSA), tetanus toxoid (TT) (Green et al., (1982) incorporated herein by reference) and keyhole limpet hemocyanin (KLH).

In preparing pharmaceutical compositions of the present invention, it may be desirable to modify the peptide antigen, or to combine or conjugate the peptide with other agents, to alter pharmacokinetics and biodistribution. A number of methods for altering pharmacokinetics and biodistribution are known to persons of ordinary skill in the art. Examples of such methods include protection of the proteins, protein complexes and polynucleotides in vesicles composed of other proteins, lipids (for example, liposomes), carbohydrates, or synthetic polymers. For example, the vaccine agents of the invention can be incorporated into liposomes in order to enhance pharmacokinetics and biodistribution characteristics. A variety of methods are available for preparing liposomes, as described in, e.g., U.S. Pat. Nos. 4,235,871, 4,501,728 and 4,837,028, each incorporated herein by reference. For use with liposome delivery vehicles, peptides are typically entrapped within the liposome, or lipid vesicle, or are bound to the outside of the vesicle.

Within certain embodiments of the invention, peptide antigens are associated with liposomes, such as lecithin liposomes or other liposomes known in the art, as a DNA-liposome mixture, or the DNA may be associated with an adjuvant known in the art to boost immune responses, such as a protein or other carrier. Additional agents which assist in the cellular uptake of DNA, such as, but not limited to, calcium ions, viral proteins and other transfection facilitating agents and methods may also be used to advantage (Wigler et al., Cell 14:725, 1978; Corsaro and Pearson, Somatic Cell Genetics 7:603, 1981; Graham and Van der Eb, Virology 52:456, 1973; Neumann et al., EMBO J. 1:841-845, 1982; and Hawley-Nelson et al., Focus 15:73-79, 1993, each incorporated herein by reference).

EXAMPLES

Materials and Methods

Preparation of peptide-pulsed DC

Human PBMC were separated from buffy coat samples of naive donors using Ficoll UNI-SEPmaxi tube. Separated cells were suspended in RPMI medium supplemented with 10% FCS, L-Glutamine, Sodium Pyruvate, MEM-EAGLE non-essential amino-acids, HEPES and Gentamycin Sulphate (Bet-Haemek Industries, IL) and cultivated for 4 h at 37° C. in a culture dish (Corning 150 mm×25 mm) Adherent cells were collected and cultured for 7 days in serum free DCCM-1 medium supplemented with L-Glutamine, huIL-4 (1000 IU/ml) (Cytolab IL) and GM-CSF-80 ug/ml (Cytolab IL). On day seven floating cells were collected and loaded with 50 ug/ml of examined peptide for 18 h at 37° C.

Development of ImMucin Specific Enriched T-Cell Clone

Thawed PBLs underwent $1^{st}$ stimulation with ImMucin pulsed Autologues DC at a ratio of 20:1 and cultured for 7 days in dedicated T cell Medium. T cell medium contained RPMI medium supplemented with 10% FCS, L-Glutamine, Sodium Pyruvate, MEM-EAGLE non-essential amino-acids, HEPES and Gentamycin Sulphate (Bet-Haemek Industries, IL) as well as with 501 U/ml of recombinant IL-7 (Cytolab IL). For the second stimulation, PBL were transferred to adherent autologues ImMucin-pulsed PBMC and cultured for additional 5 days in T cell Medium. At the end of the 5 days, medium was partial replaced with fresh medium containing 1 ug/ml of ImMucin and 50 IU/ml IL-2 for a third stimulation of 48 h at 37° C. Following the last stimulation ImMucin T cell line was checked for immune activation properties.

ELISA for Evaluation of Cytokine Secretion by Stimulated T-Cells

Cytokine release was studied during the culture of stimulated T-cells. The evaluated samples were collected from the T cell culture medium on day 2, 3, and 5 and stored until use at −20° C.

100 ml of the selected capture antibody (e.g. anti-Hu IFN-Gamma, or anti-Hu TNF-alfa or anti IL-2) were added to each well at the final concentration of 5 µg/ml in PBS. Plates were incubated for 2 h at R.T. or over night at 4° C. Next, 200 ml of blocking solution were added for an incubation of 2 h at R.T. 100 µg of evaluated samples were added in duplicate into 2 wells for 2 hours at RT. After 2 h of incubation at R.T plates were washed ×4 times in washing solution. In the next step, a Biotin-conjugated detection antibody (relevant to coated antibody) was added at a final concentration of 10 µg/ml in total volume of 1000 for 1 h at R.T. Finally, 100 µl/well working dilution (1:10000 in Blocker solution) of Streptavidin-HRP were added to each well and incubated for 1 h at R.T.

Plates were washed ×6 times with PBS-Tween (0.4%) and 100 μl/well of TMB/E Solution (CHEMICON, Catalog #ES001) was added. The plates were then exposed until blue color appeared in the wells of the positive control and no color was detected in the blank wells. To stop the color reaction, 50 μl/well of 10% of Sulfuric acid was added. The plates were counted in ELISA-Reader using a 450 nm filter.

Proliferation of Stimulated T-lymphocytes

Proliferation analysis was conducted in three different methods. In all three methods, plates were cultured for 3-5 days under visual control and then 0.5 μCu/well of 3[H] (Amersham) was added for additional culture of to 18 h at 37° C. In the last step, plates were harvested and the radioactive counts were measured in a β counter.

1. DC indirect presentation: In the first method, 100 μl of $2 \times 10^6$ thawed PBL were placed in U-shape Bottom 96 well plate (Nunc) with RPMI medium supplemented with 5% H AB serum, L-Glutamine, Sodium Pyruvate, MEM-EAGLE non-essential amino-acids, HEPES and Gentamycin. At the next stage 100 μl of $25 \times 10^4$ peptide-pulsed DC were added to each three wells of PBL and underwent proliferation analysis as described above.
2. PBL direct presentation: In the 2nd method, 100 μl of $2 \times 10^6$ PBL were placed in Flat Bottom 96 well plates (Corning) and stimulated with different concentrations (0.05 ug/ml-2 ug/ml) of peptides. In the next step the cells underwent proliferation analysis as described above.
3. PBMC direct presentation: In third method PNMC were used under similar conditions as described for the second method.

In Vitro Cytotoxic Assay (CTL)

Effector cells were ImMucin specific enriched T-Cell clone. Viable lymphocytes (effector cells), were centrifugation, resuspended in RPMI-HEPES medium, and admixed at different ratios with $5 \times 10^3$ $^{35}$S methionine-labeled, tumor cells. CTL assays were performed in U-shaped microtiter wells, at 37° C., 5% CO2 for 5 hours. Cultures were terminated by centrifugation at 1000 rpm for 10 min at 40° C. A total of 100 μl of the supematants was mixed with scintillation fluid and measured in a β counter (Becton Dickinson Can berra Australia). Percentage of specific lysis was calculated as follows: % lysis=(cpm in experimental well−cpm spontaneous release)/(cpm maximal release−cpm spontaneous release)×100. Spontaneous release was determined by incubation of 100 μl-labeled target cells with 100 μl of medium. Maximal release was determined by lysis of target cells in 100 μl 10% TrytonX-100.

FACS Analysis of T-Lymphocytes

For FACS analysis, PBLs were suspended at a final concentration of $20 \times 10^6$ and 50 μl were transfer into FACS tube (Falcon) in Blocker solution (PBS with 3% FCS and 0.1% Sodium Azide). 10 μl of fluorochrome-conjugate anti-CD4, anti-CD8, and anti-CD45RO (eBioscience) were added for 30 min on ice at 0° C. in the Dark. After the incubation cell were washed with 2 ml of the blocker solution and re suspended in 0.5 ml of Phosphate buffer saline (PBS). Samples were analyzed in a FACS-sort machine (BD) for positive florescence.

Results

SP Technology

Table 3 describes ImMucin (VLX-100) and other various VXL epitopes used in the experiments. The CTL epitopes VXL1 (D6) and VXL2 (M1.2) were used as positive controls for MUC1's SP and class I epitopes. As a control for MUC1's class I epitopes which is not derived from the SP domain, we have used the previously identified CTL epitopes VXL6 (M1.1). We also used CTL epitopes derived from the SP domains of other non MUC1 TAA like Her2/neu (VXL-8) or Tyrosinase (VXL-11). As a positive control for class II epitope we used the universal pan-class II epitope peptide PADRE (VXL-14).

TABLE 3

ImMucin and other target epitopes used in the experiments

|  | ID | Previous ID | Sequence | Target | Alleles Class I (binding) | Alleles Class II (binding) |
|---|---|---|---|---|---|---|
| 1 | VXL01 | Muc-D6 | LLLTVLTVV | MUC-1 SP | A0201, A0205 B62, B52.1 | DRB107 |
| 2 | VXL02 | C6, M1.2 | LLLLTVLTV | MUC-1 SP | A0201, A0205 | DRB101, 3, 4, 11, 13, 15 |
| 3 | VXL04 |  | TQSPFFLLL | Other MUC-1SP | A0201, 5 B60, B62 B27.2, 5 B37.1 B39. Cw3.1 | ND |
| 4 | VXL05 |  | SPFFLLLLL | Other MUC-1SP | B14 B60 B7 B27.5 B39.1 B51.1, 2 Cw4.1, 6.2, | ND |
| 5 | VXL06 | M1.1 | STPPVHNV | MUC-1 none SP | A0201 | ND |
| 6 | VXL08 | Her2/neu ND | ALCRWGLLL | Her2/neu SP | A0201, B27.5 | ND |
| 7 | VXL11 | Tyrosinase ND | MLLAVLYCL | Melanoma SP | A0201, 0205, B27.5, CW3.1 | DRB10701, 3, 15.1, 15.6, DRB50101 |
| 8 | VXL12 | POL-ND | ILKEPVHGV | HIV non SP | A0201 | DRB1 0421 |
| 9 | VXL14 | PAN-DR | PADREAGVAAWTLKAAA | ND | ND | Various Class II |
| 10 | VXL-101 |  | MWATQGLAVALALSVLPGSRA | SP Armet | A24, A68.1 B7, B51.1, C4.1, C6.2, DR0301, 0901, 15, 13, 7, 9 | DR0301, 0901, 15, 13, 7, 9 |
| 11 | VXL-102 |  | MAARAVFLALSAQLLQA | SP BAGE | A24, A2.1.B7, B8, B35.1, B58.1, C4.1, C6.2, | DR0301, 0901, 47, 1, 9 |
| 12 | VXL-100 | ImMucin | MTPGTQSPFFLLLLLTVLTVV | MUC-1 SP | A24, A2.1.B7, B35.1, B51 B58.1, C7.2, C4.1, C6.2 | DR0 1501, 301, 1101, 701, 401, 1302, 0901 |

Proliferation Properties Indicated by Stimulation Index (SI)

In the first set of experiments, the 21mer ImMucin, its different 9mer epitopes and other control epitopes (Table 3) were evaluated in proliferation assays with the aim of finding their optimal mode of presentation, stimulated dose as well as their peak of activity (time wise).

To evaluate the most efficient method for priming of PBLs with the different peptides, the following methods were compared:

a. In-direct presentation of the peptide via Autologues—pulsed DC b. Direct presentation of the peptides via PBMC i.e. monocytes
c. Direct presentation of peptides to PBL without any APC Proliferation analysis is usually indicating the existence of specific T cells activation mainly CD4+ but could also be associated with CD8+ activation.

Five experiments were performed according to the protocol described in material and methods with buffy-coat enriched PBLs obtained from six different naive donors (obtained from the Israeli blood bank).

The most immunogenic antigen is the 21mer ImMucin which manifested a SI, of 4 and 2 respectively for peptide presentation via DC and PBMC (see table 4). In general, SI of ≥2 is considered to be a strong specific activation. The high SI of ImMucin obtained with naive PBLs which didn't have any prior priming by ImMucin in vivo, i.e. the first and only antigen-T cell interaction occurred in-vitro, is a positive indication of the high immunodominant properties of ImMucin.

There was no activation of PBL when ImMucin (or other epitopes) were presented directly to PBL without APC, suggesting that ImMucin's activity is not mediated via a non-specific mitogen-like mechanism of action but rather it needs a specific intracellular process for efficient presentation via a proper APC. Moreover, it is clear that presentation via professional APC i.e. Dendritic Cells is better than presentation via monocytes from PBMC since stimulation of PBMC with peptides, gave a weaker effect (Table 4).

Since the experiments were carried out on six different donors, each one of them having an individual repertoire of Class I and II alleles, the high SI of ImMucin suggests polyclonal T cell activation via binding to multi MHC epitopes. In other words, different epitopes are used in different donors. To further examine this issue, the index of stimulation for ImMucin's 9mer epitopes was analyzed. Like ImMucin, the class I and/or class II 9mer epitopes VXL-4, VXL-1 and VXL-5 (see Table 4 and 3) manifested high stimulation index of SI>3. This activity is probably not restricted to a single class I or II allele, since these peptides do not share the same MHC binding properties as can be seen in the case of XVL-5 which does not bind the HLA-A2.1 allele like the epitopes VXL-4, VXL-1. Another ImMucin epitope, the 9mer VXL-2, manifested moderate SI scores of 2.2 although it was shown in the past to be a highly potent class I, HLA-A2.1-restricted CTL epitope. It is possible that in this assay the activation of CD4+ rather than CD8+ was more dominant. Other SP derived epitopes like the Her2/Neu or Tyrosinase, and the MUC1 non SP-epitope showed moderate activation of 1.5<SI<2.

TABLE 4

Proliferation analysis of PBL using ImMucin and other VXL target epitopes indicated by Index of stimulation (SI). SI is calculated by dividing the CPM obtained in an analyzed sample to the CPM obtained in a control sample. Results are representative of 5 similar experiments.

| Evaluated antigens | | PBL Index of stimulation (SI) | | |
|---|---|---|---|---|
| Name | Origin | via DC | Direct no APC | via PBMC |
| ImMucin | 21mer MUC1 SP | 4 | 0 | 2.0 |
| VLX-1 | 9mer MUC1 SP | 3.2 | 0 | 1.59 |
| VXL-2 | 9mer MUC1 SP | 2.2 | 0 | 1.2 |
| VXL-4 | 9mer MUC1 SP | 3.74 | 0 | 1.45 |
| VXL-5 | 9mer MUC1 SP | 3.73 | 0 | 1.8 |
| VXL-6 | 9mer MUC1 non SP | 1.76 | 0 | 1.53 |
| VXL-8 | 9mer Her2/neu SP | 1.75 | 0 | 1.5 |
| VXL-11 | 9mer Tyrosinase SP | 1.65 | 0 | 1.25 |

Analyzing the Time for Maximal Peak of PBL Activation

TABLE 5

Analyzing the maximal peak of PBL activation (in a proliferation assay), following stimulated with ImMucin and other VXL-peptides. Observation was done daily during 5 days by visual inspection using light microscopy. Maximal peak of PBL activation is determined when <50% of the PBLs appear in clumps. Results are the average of 5 experiments.

| Evaluated antigens | | Peak of Proliferation (Hours) | | |
|---|---|---|---|---|
| Name | Origin | via DC | Direct no APC | via PBMC |
| ImMucin | 21mer MUC1 SP | 96 h | No proliferation | 120 h |
| VXL-1 | 9mer MUC1 SP | 120 h | No proliferation | 120 h |
| VXL-2 | 9mer MUC1 SP | 120 h | No proliferation | 120 h |
| VXL-4 | 9mer MUC1 SP | 72-96 h | No proliferation | 72-96 h |
| VXL-5 | 9mer MUC1 SP | 48-72 h | No proliferation | 48-72 h |
| VXL-6 | 9mer MUC1 non SP | 120 h | No proliferation | 120 h |
| VXL-8 | 9mer Her2/neu SP | 120 h | No proliferation | 120 h |
| VXL-11 | 9mer Tyrosinase SP | 96 h | No proliferation | 96 h |

A different parameter for assessing the properties of ImMucin and the other VXL-peptide epitopes is by analyzing the time until a maximal peak of activity occurs and the optimal dose for maximal stimulation. Maximal peak of PBL activation is determined when <50% of the PBLs appear in clumps. In these experiments, the kinetic (time) in the proliferation of lymphocytes from the six naive donors stimulated at a fix dose of 0.05-1 ug/ml by ImMucin and other VXL-Peptides, was observed.

A different profile for maximal peak of proliferation (i.e. stimulation property) and optimal dose for proliferation was found when comparing different peptide epitopes. Results in the five experiments show a more rapid peak of proliferation to VXL-4 and VXL-5 with a peak at 48-72 hours (Table 5) and lowest concentration needed for activation 0.2-0.05 ug/ml (Table 6) while ImMucin and other SP-derived epitopes or non SP epitope gave slower peak of proliferation at the range of 96 hours and a slightly higher dose for stimulation 0.05-1 ug/ml (Table 6). Interestingly, the ImMucin CTL epitopes VXL1 and VXL2 as well as the Her2/Neu CTL epitope manifested in these experiments peak for maximum stimulation at 120 hours with a slightly higher dose 0.05-1 ug/ml although their MHC binding affinity are as high as those of VXL-4 and VXL-5 (data is not presented). Nevertheless, when comparing the results in this set of experiments (Table 5, 6) to those obtained in the proliferation assay (Table 4), it appears that the rapid peak of activation of VXL-4 and VXL-5 does not always positively correlate with their high SI. It is therefore assumed that at least part of this phenomenon is associated with the unique properties of sequences within the signal peptides (SP). In particular, SP-associated sequences/epitopes were noted, e.g. the MUC1 VXL1, 2, and 4 epitopes, but also other SP epitopes such as VXL 8 and VXL11, which contain antigen specific properties for CD4+ and/or CD8+ activation and other sequences (such as VXL-4 and VXL-5) which in addition to CD4+ and/or CD8+ activation also have an "adjuvant like" activity. The adjuvant-like property of signal peptides was already shown in the past by attaching SP to other non-SP epitopes in order to increase their immunity (Sherritt et al., 2001). The relatively slower peak of activity of ImMucin and VXL-1, 2, 6, and 8 can potentially be associated with the time needed for them to enter the APC and move from the Class II compartment into the Class I compartment in a process known as "cross presentation" or "cross priming". It is known that exogenous antigens can gain entry into the so-called endogenous pathway using the cross-presentation mechanism which is known to be very effective for class I-restricted cytotoxic T lymphocyte (CTL) epitopes.

The effect of Dose on PBL Activation

TABLE 6

Analyzing the optimal dose of ImMucin and other VXL-peptides required for PBL activation (in a proliferation assay). Observation was done daily during 5 days by visual inspection using light microscopy. Results are the average of 5 experiments using six different donors.

| Evaluated antigens | | Optimal dose | | |
|---|---|---|---|---|
| Name | Origin | via DC | Direct no APC | via PBMC |
| ImMucin | 21mer MUC1 SP | 12.5-25 × 10e6/well | No Influence | 0.05-1 ug/ml |
| VLX-1 | 9mer MUC1 SP | 12.5-25 × 10e6/well | No Influence | 0.05-1 ug/ml |
| VXL-2 | 9mer MUC1 SP | 12.5-25 × 10e6/well | No Influence | 0.05-1 ug/ml |
| VXL-4 | 9mer MUC1 SP | 12.5-25 × 10e6/well | No Influence | 0.2-0.05 ug/ml |
| VXL-5 | 9mer MUC1 SP | 12.5-25 × 10e6/well | No Influence | 0.2-0.05 ug/ml |
| VXL-6 | 9mer MUC1 non SP | 12.5-25 × 10e6/well | No Influence | 0.05-1 ug/ml |
| VXL-8 | 9mer Her2/neu SP | 12.5-25 × 10e6/well | No Influence | 0.05-1 ug/ml |
| VXL-11 | 9mer Tyrosinase SP | 12.5-25 × 10e6/well | No Influence | 0.05-1 ug/ml |

ELISA Assay for Studying Cytokine Release by Stimulated PBL

One of the important parameters of activated T cells is their secretion of key cytokines like TNF-Alfa, IL-2 and IFN-gamma as an outcome of antigen stimulation. Secretion of a given cytokine is highly dependent on the type of secretory cell, CD4+ vs. CD8+ and on the stage of activation, in particular early vs. late activation. TNF-Alfa is a proinflamatory cytokine which is secreted at early stage of activation by both CD4+ and CD8+. Interleukin-2 is one of the key cytokines which enhance the proliferation of CD4+ T lymphocytes. It induces a secondary immune response of CD8+ cells and the development of memory CD8+ cells following primary activation with antigen. Therefore, IL-2 is usually associated with late secretion. IFN-gamma is produced mainly by CD8+ T cells following IL-2 secretion (late secretion) and is correlates with CD8+ specific activation and function.

Hence, the cytokine profile released by T-Lymphocytes stimulated once (Table 7) or several times (FIG. 1) with ImMucin or other VXL 9mer epitopes was studied using an ELISA assay according to the protocol described in material and methods.

TABLE 7

ELISA quantitative assay for Cytokine secretion profiles of PBL stimulated once with ImMucin or other VXL 9mer epitopes DC at the ratio of 16:1. The results represent one out of five experiments using six different donors. SI of the peptides is also indicated.

| | TNF-Alfa | | IFN-gamma | | IL-2 | |
|---|---|---|---|---|---|---|
| Evaluated antigens | IS | ng/ml | IS | ng/ml | IS | ng/ml |
| ImMucin | 4 | 11.6 | 4 | 0.5 | 4 | 3.62 |
| VXL-1 | 3.2 | 11.1 | 3.2 | 0 | 3.2 | 0 |
| VXL-2 | 2.2 | 0 | 2.2 | 0 | 2.2 | 0 |
| VXL-4 | 3.4 | 17.1 | 3.4 | 0 | 3.4 | 0 |
| VXL-5 | 3.74 | 14.8 | 3.74 | 0 | 3.74 | 5 |
| VXL-6 | 1.76 | 0 | 1.76 | 0 | 1.76 | 0 |
| VXL-11 | 1.65 | 12.8 | 1.65 | 0 | 1.65 | 0 |

As envisaged, a single stimulation resulted in the early secretion of TNF-Alfa, produced by both CD4+ and CD8+. The antigens which induced the highest cytokine release are the 9mers VXL4 and VXL5; the 21 mer ImMucin also revealed a high level of TNF-Alfa secretion of 11.6 ng/ml. Also, VXL-11 which didn't perform well in the proliferation analysis also secreted high amounts of TNF-Alfa. The results of ImMucin's cytokine secretion are directly correlated with the high SI of ImMucin, SI=4 (see table 7). IL-2 secretion of 3.62 ng/ml was also observed. This secretion is probably performed by CD4+ T cells activated with the ImMucin vaccine, as this phenomenon is usually associated with multiple activations and with the induction of memory. Lastly, ImMucin was the only antigen which could induce the secretion of IFN-Gamma by CD8+ T cells. The results showing IFN-Gamma and IL-2 secretion emphasize the "super activation" properties of ImMucin which can induce a polyclonal activation via a combination of multiple epitopes for both CD4+ and CD8+ on one sequence. This property seems to compensate in this experiment for the lack of repeated activation. Additional support for this assumption is provided by the high level (ng/ml) of cytokine release from the naive T cells, which are usually if at all, at the range of pg/ml (i.e. three folds lower). Other ImMucin SP epitopes like VXL-1, VXL-4 and VXL-5 as well as other SP epitopes like VXL-11 showed also high TNF-Alfa release which mostly correlates with the high SI of these epitopes. The high IL-2 secretion by VXL-5 together with the other results obtained for this epitope suggest that it may work as a CD4+ epitope which may be responsible for some of the IL-2 secretion induced by ImMucin.

Cloning of Specific T-cells

In the first set of experiments the immunogenic properties of ImMucin and its VXL epitopes were demonstrated with respect to CD4+ and CD8+ T cells. In the following set of experiments the ability of ImMucin to undergo a process of cross priming is demonstrated. During this process, the 21mer is entering the APC via the class II compartment, processed into the class I compartment and finally presents its different VXL 9mer epitopes, namely 1, 2, 4 and 5 by different MHC class I and/or II molecules. Also demonstrated is the ability of ImMucin specific clones to lyse MUC1 expressing tumor cells.

For that purpose, an enriched ImMucin-specific T cell subpopulation was produced via repeated stimulation with ImMucin. The specificity of the subpopulation for ImMucin, as well as to the other VXL epitopes, was examined using proliferation assays, cytokine release assays, FACS analysis in which the percentage and type of cells enriched during the enrichment process was analyzed, and using a CTL assay against selected target cells.

For producing the specific T cell subpopulation PBL were stimulated three times for 7, 5 and 2 days with ImMucin presented via DC and PBMC. Following the 3$^{rd}$ stimulation the cells were evaluated against the different VXL epitopes.

Analyzing the levels of cytokine release during the development process of the T cell clone revealed, as expected, a high peak of TNF-Alfa secretion (5 ng/ml) during the first stimulation with ImMucin (FIG. 1). Following a second stimulation with ImMucin, the levels of TNF-Alfa secretion decreased and TNF-Alfa secretion completely disappeared after the 3$^{rd}$ stimulation on day 14. On the contrary, the secretion levels of IL-2 from CD4+ T cells and INF-gamma mainly from CD8+ T cells have increased dramatically after the second and third stimulations with ImMucin suggesting an enrichment of CD4+ and CD8+ cells with potentially higher specificity as killer cells (high IFN-gamma secretion) with memory (IL-2 secretion). This unique and novel dual specificity of CD4+ and CD8+ subpopulations to ImMucin, may be explained by the nature of this peptide vaccine harboring both class I and II immunodominant epitopes. Similar to the results obtained in the initial experiment (Table 7) also in this experiment the levels of secretion are high at the range of ng/ml.

Figure 2:
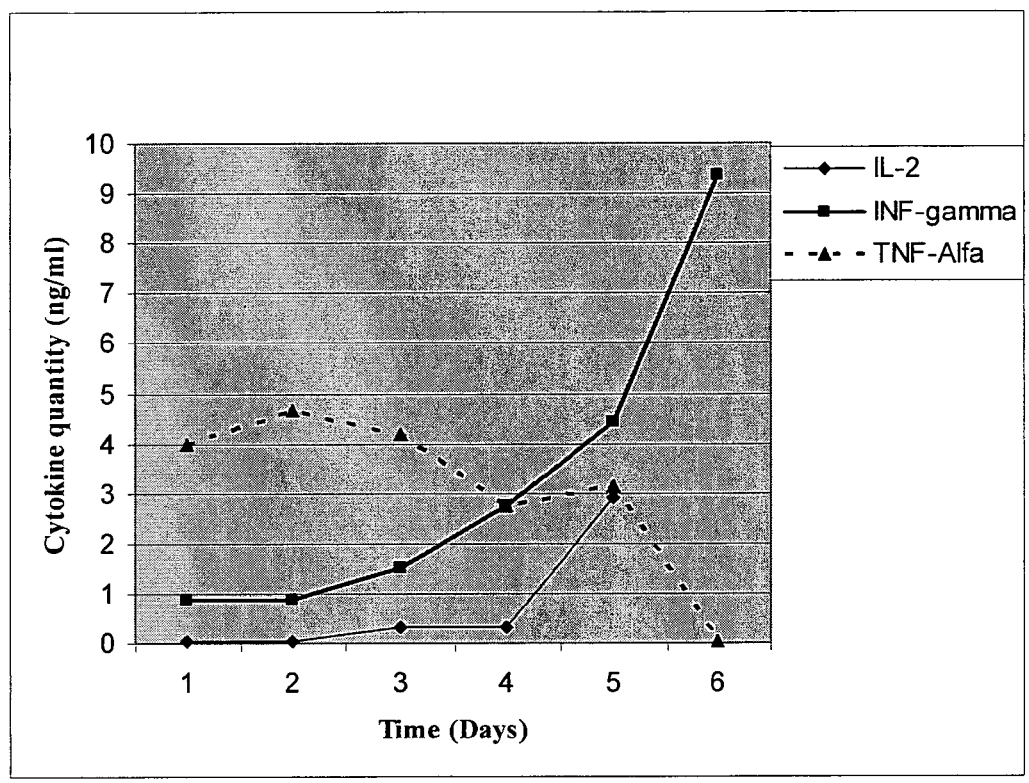
FIG. 2 is a graph showing FACS analysis of T cell phenotype evaluation during consistent stimulation with ImMucin. The Results represent one out of two experiments using four different donors.

The ability of ImMucin to propagate a subpopulation of CD4+ and CD8+ T cells was further analyzed, and in particular the ability of ImMucin to transform naive CD4+ and CD8+ T cells into memory cells. This property was evaluated in a FACS analysis measuring the CD45RO+ marker for memory T cells on CD4+ and CD8+ subpopulations (FIG. 2).

As can be seen in this particular experiment, repeated stimulation with ImMucin transformed PBLs into CD4+ and CD8+ T cells. In both cases, a two fold increase, from 43% to 85% in the case of CD4+ and from 15% to 36% in the case of CD8+ T cells. These numbers represent the normal CD4+ CD8+ percentage ratio and suggest a dual activation of both T cell subpopulations. ImMucin activation also increases by two fold the percentage of memory CD45RO+ cells which are the cells that were effectively primed with ImMucin and will remain as memory cells. It is important to note that although the percentage of memory cells did not increase after the first stimulation (FIG. 2) their total numbers do increase (data is not presented).

Next, the ability of ImMucin to undergo cross priming and present its different epitopes for inducing T cell proliferation was explored. As can be seen in Table 8 each one of the MUC1 SP epitopes VXL1, VXL2, VXL4 and VXL5 induced a specific proliferation with an average IS ranging from 2.66 to 3.5 which was comparable to the SI achieved using ImMucin itself. VXL-11, the SP epitope which is not deduced from the MUC1 antigen and VXL-6 which is a MUC1 epitope which is not deduced form the SP domain manifested lower SI with an average SI of 1.14-1.125 or 2-5 times lower than the MUC1 SP epitopes. Some background was expected for VXL6 and VXL-11 as they do harbor epitopes from other SP-sequences or from MUC1 sequences.

The cytokine profile obtained from the specific T cell subpopulation stimulated with the MUC1 SP epitopes VXL1, VXL2, VXL4 and VXL5 conform to the proliferation results, showing again that antigen specificity is positively correlated with cytokine release (Table 9). ImMucin and its SP epitopes VXL1, VXL2, and VXL4 manifested high IL-2 and IFN-gamma secretion compared to low to moderate levels induced by the other epitopes. The secretion of TNF-Alfa which is less specific and appears in an early stage is high in all the epitopes tested. The positive results achieved in this experiment are unique compared with results obtained with class I peptide vaccines since in this experiment ImMucin was not matched with the relevant HLA alleles of the donors and still received a positive proliferation.

TABLE 8

Proliferation of a specific T-cell subpopulation which underwent three stimulations with ImMucin or different VXL-peptides as assessed in a proliferation assay. Results represent one out of two experiments using four donors.

| Evaluated antigens | IS (Range) | IS (Average) |
| --- | --- | --- |
| ImMucin | 2.2-4.2 | 3.2 |
| VXL-1 | 1.66-4.4 | 3.05 |
| VXL-2 | 1.45-5.1 | 3.275 |
| VXL-4 | 2.4-2.93 | 2.665 |
| VXL-5 | 2.75-4.4 | 3.575 |
| VXL-6 | 1-1.25 | 1.125 |
| VXL-11 | 1-1.28 | 1.14 |

TABLE 9

ELISA quantitative assay for Cytokine secretion profiles of T-Cell specific subpopulation (Clones) stimulated with ImMucin and various VXL-Peptides. The results represented summary of two experiments using four donors.

| | TNF-Alfa | | INF-gamma | | IL-2 | |
| --- | --- | --- | --- | --- | --- | --- |
| Evaluated antigens | % of clones | Range ng/ml | % of clones | Range ng/ml | % of clones | Range ng/ml |
| ImMucin | 90 | 2.7-8.9 | 90 | 2.3-11.8 | 83 | 2-11.4 |
| VXL1 | 83 | 2.7-9.8 | 33 | 1.4-8.9 | 83 | 3.3-10.7 |

TABLE 9-continued

ELISA quantitative assay for Cytokine secretion profiles of T-Cell specific subpopulation (Clones) stimulated with ImMucin and various VXL-Peptides. The results represented summary of two experiments using four donors.

| Evaluated antigens | TNF-Alfa | | INF-gamma | | IL-2 | |
|---|---|---|---|---|---|---|
| | % of clones | Range ng/ml | % of clones | Range ng/ml | % of clones | Range ng/ml |
| VXL-2 | 83 | 1.9-9.4 | 25 | 1.4-8.9 | 50 | 2.53-10.2 |
| VXL-4 | 58 | 3.1-9.8 | 33 | 2.6-8.4 | 33 | 3.8-8.7 |
| VXL-5 | 50 | 3.84-9.2 | 33 | 2.75-5.5 | 0 | 0 |
| VXL-6 | 50 | 7.56-11.4 | 8.3 | 3.25 | 0 | 0 |
| VXL-11 | 0 | 0 | 33 | 2.2-4.7 | 0 | 0 |

In order to further evaluate the class II/class I cross presentation as well as the specificity and function of the T-cell clones, their class I restricted lysis potential was analyzed. For this assay the clones were screened for Class I HLA-A2.1 expression and their potential to lyse MUC1 and HLA-A2.1 positive and negative cell-lines was evaluated. Based on this evaluation two clones which were found to express the HLA-A2.1 allele was selected. The results summarized in Table 10 show a MUC1 as well as HLA-A2.1-restricted lysis. A breast tumor cell such as MDA-MB-231 which expresses both MUC1 and HLA-A2.1 was lysed effectively (23%), while another breast tumor cell line MDA-MB-468 which expresses only MUC1 but not the HLA-2.1 was not lysed al all. Other control cell-lines didn't manifest any lysis (see table 10).

These results demonstrate several important properties of ImMucin which are important for an effective vaccine:
1. Cross presentation of ImMucin by host APC in the correct manner. Processing, expression, and presentation of ImMucin's epitopes by APC to lymphocytes.
2. The processing, expression, and presentation of ImMucin's epitopes on MUC1 positive tumor cells.
3. The immunodominance of ImMucin as an effective inducers of CTL activation via CD8+.

In summary, out of 14 different blood samples derived from naive donors, in 12 ImMucin specific activation could be observed. It is therefore clear that ImMucin is able to induce antigen specific CD4+ as well as CD8+ T cell activation which can lead to effective anti-tumor vaccine properties including lysis, cytokine release and memory in the majority of the population.

TABLE 10

CTL assay of HLA-A2.1 positive T-Cell specific sub-population (Clone) stimulated with ImMucin. MUC1 expression (+ represents low, +++ represents high) was measured by the H23 anti-MUC1 mAb. HLA-A21 expression was measured using the BB7.7 mAb. The results represent two separate experiments using two different donors.

| Cell Line | Origin | MUC1 expression | HLA-A2.1 restriction | Lysis % (1:50) |
|---|---|---|---|---|
| MDA-MB-231 | Human Brest Carcinoma | +++ | + | 23 |
| MDA-MB-486 | Human Brest Carcinoma | ++ | − | 0 |
| K562 | Human Myalo Leukeima | + | − | 1.7 |
| HT-29 | Human Colon Carcinoma | − | − | 0 |
| Molt-4 | Human T cell Leukemia | − | − | 1.1 |

The Immunodominance of Other SP Vaccine

Immunogenic properties of SP-derived sequences were observed in all the experiments conducted using MUC1 and non-MUC1 derived peptides. Part of the immunity is antigen specific while part of it is more SP specific. These observations were supported by the in-silico algorithm which predicted the existence of immunodominant SP epitopes derived from novel as well as known TAA which manifested potential binding to both Class I and Class II epitope in over 50% of the population (cross HLA).

In order to verify the in-silico predictions, two additional tumor associated SP vaccines were synthesized. The first one VXL102 (SEQ ID NO. 7) is derived from the known melanoma associated TAA BAGE while the second VXL101 (SEQ ID NO 1) is derived from a novel protein, ARMET which is known to be overexpressed in certain tumors. The immunodominant properties of these two peptides and in particular their ability to stimulate T cells in a proliferation assay, were examined.

PBL from two healthy donors were stimulated with VXL-102 or VXL-101 peptides. As a positive control for class II activation the universal pan-class II epitope peptide PADRE (VXL-14) was used. As can be seen ImMucin and Armet manifested the highest SI in this experiment which was equivalent to the SI obtained with the universal PAN DR epitope VXL-14 (Table 11). Since the later is considered to be a very immunogenic peptide which is added to many vaccines for PAN CD4+ T cell activation, the comparable SI obtained in the experiment is an important finding which stresses the high immunodominant properties of both ImMucin and ARMET. In this experiment VXL-102 manifested lower SI than VXL-101 and ImMucin but still higher than the non-SP epitope VLX-6. A similar pattern of results was obtained in ELISA assay analyzing the cytokine profile of the peptide-activated T cells (Table 12). While all peptides induced high secretion levels of TNF-Alfa (<10 ng/ml), only ImMucin induced IL-2 and VXL-101 induced INF-Gamma suggesting that enrichment of CD4+ and CD8+ T cells occurred. As in the proliferation experiment VXL-102 didn't induced IL-2 or IFN-gamma production. This moderate immunogenic profile could be associated with the HLA match of the two donors used in this experiment.

TABLE 11

Index of stimulation for PBL by VXL-Peptides. Results represent an average of two donors.

| Evaluated antigens | | PBL Index of stimulation SI | |
|---|---|---|---|
| Name | Target Ag | via DC | Direct no APC |
| ImMucin | MUC1 | 2.8 | 0 |
| VXL-14 | Universal Pan DR | 2.94 | 0 |
| VXL-101 | ARMET | 2.8 | 0 |

TABLE 11-continued

Index of stimulation for PBL by VXL-Peptides.
Results represent an average of two donors.

| Evaluated antigens | | PBL Index of stimulation SI | |
|---|---|---|---|
| Name | Target Ag | via DC | Direct no APC |
| VXL-102 | BAGE | 1.9 | 0 |
| VXL-6 | MUC1 non SP | 1.44 | 0 |

TABLE 12

ELISA quantitative assay for Cytokine secretion profiles of PBL stimulated once with ImMucin and two additional tumor associated SP vaccinesVXL-101 and VXL-102 The results represent stimulation with peptide pulsed DC in ratio 16:1 one out of two experiments using two different donors.

| Evaluated antigens | TNF-Alfa | | IFN-gamma | | IL-2 | |
|---|---|---|---|---|---|---|
| | IS | ng/ml | IS | ng/ml | IS | ng/ml |
| ImMucin | 2.8 | 11.6 | 2.8 | 0.5 | 2.8 | 3.62 |
| VXL-101 | 2.8 | 10.5 | 2.8 | 1.1 | 2.8 | 0 |
| VXL-102 | 1.9 | 15.5 | 1.9 | 0 | 1.9 | 0 |

REFERENCES

Boel P. et al Immunity, 2 (2): 167-175 (1995)
Brossart P, Heinrich K S, Stuhler G, Behnke L, Reichardt V L, Stevanovic S, Muhm A, Rammensee H G, Kanz L, Bragger W. Identification of HLA-A2-restricted T-cell epitopes derived from the MUC1 tumor antigen for broadly applicable vaccine therapies. *Blood.* 93(12): 4309-17 (1999).
Cannon L, El-Shami K M, Paz A, Pascolo S, Tzehoval E, Tirosh B, Koren R, Feldman M, Fridkin M, Lemonnier F A, Eisenbach L. Novel breast-tumor-associated mucin-derived peptides: characterization in $D^{b-/-}$ x$\beta$2 microglobulin ($\beta$2m) null mice transgenic for a chimeric HLA-A2.1/$D^b$-$\beta$2 microglobulin single chain. *Int. J. Cancer.* 85, 391-397 (2000).
Chaux, P., V. Vantomme, V. Stroobant, K. Thielemans, J. Corthals, R. Luiten, A. M. Eggermont, T. Boon, and P. Van der Bruggen. Identification of MAGE-3 epitopes presented by HLA-DR molecules to CD4(+) T lymphocytes. *J. Exp. Med.* 189, 767-78 (1999).
Christopher E, Touloukian, Wolfgang W. Leitner, Suzanne L. Topalian, Yong F. Li, Paul F. Robbins, Steven A. Rosenberg and Nicholas P. Restifo. Identification of a MHC Class II-Restricted Human gp100 Epitope Using DR4-IE Transgenic Mice. *The Journal of Immunology,* 164, 3535-3542 (2000).
Dayhof, M. D., Atlas of protein sequence and structure, *Nat. Biomed. Res. Found.* 5, suppl. 3 (1978)
Fisk, B., Blevins, T. L., Tylor-Wharton, J. and Ionnides, C. G., Identification of an immunodominant peptide of HER2/neu protooncogene recognized by ovarian tumor specific cytotoxic T-lymphocyte lines. *J exp. Med.* 181, 2109-2117 (1995).
Fung, P. Y. and Longenecker, B. M., Specific immunosuppressive activity of epiglycanin, a mucin-like glycoprotein secreted by a murine mammary adenocarcinoma (TA3-HA). *Cancer Res.* 51, 1170-1176 (1991).
Gilboa Eli., The promise of cancer vaccines *Nature Reviews* 4, 401-411 (2004).
Graham, R. A., Burchell, J. M. and Taylor-Papadimitriou, J., The polymorphic epithelial mucin: potential as an immunogen for a cancer vaccine. *Cancer Immunol. Immunother.* 42, 71-80 (1996).
Grulich et al., Lancet 370, 59 67 (2007)
Green et al., Cell 28:477, 1982
He X, Tsang T C, Luo P, Zhang T, Harris D T. Enhanced tumor immunogenicity through coupling cytokine expression with antigen presentation. *Cancer Gene Ther.* 10(9), 669-77 (2003).
Ho, S. B., Niehans, G. A., Lyftogt, C., Yan, P. S., Cherwitz, D. L., Gum, E. T., Dahiya, R. and Kim, Y. S., Heterogeneity of mucin gene expression in normal and neoplastic tissues. *Cancer Res.* 53, 641-651 (1993).
Hung K, Hayashi R, Lafond-Walker A, Lowenstein C, Pardoll D, Levitsky H. The central role of CD4(+) T cells in the antitumor immune response. *J. Exp. Med.* 188, 2357-2368 (1998).
Jaeger E, Bernhard H, Romero P, Ringhoffer M, Arand M, Karbach J, Ilsemann C, Hagedorn M, Knuth A. Generation of cytotoxic T-cell responses with synthetic melanoma-associated peptides in vivo: implications for tumor vaccines with melanoma-associated antigens. *Int. J. Cancer.* 66, 162-169 (1996).
Kast, W. M., Brandt, R. M. P., Sidney, J., Drijihout, J. W., Kubo, R. T., Melief, C. J. M. and Sette, A. Role of HLA-A motifs in identification of potential CTL epitopes in human papillomavirus type 16 E6 and E7 proteins. *J Immunol* 152: 3904-3912 (1994)
Kedar, E. and Klein, E. Cancer Immunotherapy: Are the results discouraging? Can they be improved? *Adv Immunol* 58:245-322 (1995).
Knutson K L, Schiffman K, Disis M L. Immunization with a HER-2/neu helper peptide vaccine generates HER-2/neu CD8 T-cell immunity in cancer patients. *J Clin Invest.* 107(4): 477-84 (2001)
Lenstra et al., Arch. Virol., 110, 1-24 (1990)
Lipman and Pearson, Science 227, 1435-1441 (1985).
Mandelboim, O., G. Berke, M. Fridkin, M. Feldman, M. Eisenstein, and L. Eisenbach. CTL induction by a tumor associated antigen octapeptide derived from a murine lung carcinoma *Nature.* 369, 67-71 (1994).
Mandelboim, O., E. Vadai, M. Fridkin, A. Katz-Hillel, M. Feldman, G. Berke, and L. Eisenbach. Regression of established murine carcinoma metastases following vaccination with tumor-associated antigen peptides *Nat. Med* 11, 1179-83 (1995).
Manici, S., T. Sturniolo, M. A. Imro, J. Hammer, F. Sinigaglia, C. Noppen, G. Spagnoli, B. Manzi, M. Bellone, P. Dellabona, and M. P. Protti. Melanoma cells present a MAGE-3 epitope to CD4(+) cytotoxic T cells in association with histocompatibility leukocyte antigen DR11. *J. Exp. Med* 189, 871-6 (1999).
Marchand, M., Weynants, P., Rankin, E., Arienti, F., Belli, F., Parmiani, G., Cascinelli, N., Bourland, A., Wanwijck, R., Humblet, Y., Canon, J. L., Naeyaert, J. M., Plagne, R., Deraemaeker, R., Knuth, A., Jager, E., Brasseur, F., Herman, J., Coulie, P. G. and Boon, T. *Int. J. Cancer* 63:883-885 (1995)
McGuckin, M. A., M. D. Walsh, B. G. Hohn, B. G. Ward, and R. G. Wright. Prognostic significance of Muc-1 epithelial mucin expression in breast cancer. *Hum Pathol* 26, 432-439 (1995).
Minev B R, Chavez F L, Dudouet B M and Mitchell M S. Synthetic insertion signal sequences enhance MHC class I presentation of a peptide from the melanoma antigen MART-1. *Eur J Immunol.* (8):2115-24. (2000)

Morein et al., *Nature* 308:457 (1984)

Pardoll, D. M., and S. L. Topalian. The role of CD4+ T cell responses in antitumor immunity. Curr. Opin. Immunol. 10, 588-94 (1998).

Rammensee, H.-G., Falk, K. and Rotzschke, O. Peptides naturally presented by MHC class I molecules. *Annu Rev Immunol* 11:213-244 (1993)

Ras, E., van der Burg, S. H., Zegveld, S. T., Brandt, R. M., Kuppen, P. J., Offringa, R., Warnarr, S. O., van de Velde, C. J. and Melief, C. J., Identification of potential HLA-A *0201 restricted CTL epitopes derived from the epithelial cell adhesion molecule (Ep-CAM) and the carcinoembryonic antigen (CEA). *Hum. Immunol.* 53, 81-89 (1997).

Rhodes D R and Chinnaiyan A M. Integrative analysis of the cancer transcriptome. *Nature genetics.* 37 Suppl: S31-7 (2005)

Rosenberg S A, Yang J C, Schwartzentruber D J, Hwu P, Marincola F M, Topalian S L, Restifo N P, Dudley M E, Schwarz S L, Spiess P J, Wunderlich J R, Parkhurst M R, Kawakami Y, Seipp C A, Einhorn J H, White D E. Immunologic and therapeutic evaluation of a synthetic peptide vaccine for the treatment of patients with metastatic melanoma. *Nat. Med.* 4, 321-327 (1998).

Rosenberg S A, Yang J C, Restifo N P. Cancer immunotherapy: moving beyond current vaccines. *Nat Med.* 10 (9):909-15 (2004)

Sherritt M, Cooper L, Moss D J, Kienzle N, Altman J and Khanna R. Immunization with tumor-associated epitopes fused to an endoplasmic reticulum translocation signal sequence affords protection against tumors with down-regulated expression of MHC and peptide transporters. *Int. Immunol.* (3):265-71 (2001)

Shridhar R. et al., Cancer Res. 56 (24) 5576-5578

Townsend, A. and Bodmer, H. Antigen recognition by class I-restricted T lymphocytes. *Annu Rev Immunol* 7: 601-624 (1989)

Treon S P, Maimonis P, Bua D, Young G, Raje N, Mollick J, Chauhan D, Tai Y T, Hideshima T, Shima Y, Hilgers J, von Mensdorff-Pouilly S, Belch A R, Pilarski L M, Anderson K C. Elevated soluble MUC1 levels and decreased anti-MUC1 antibody levels in patients with multiple myeloma. *Blood* 96; 3147-53 (2000)

Weber J S, Hua F L, Spears L, Marty V, Kuniyoshi C, Celis E. A phase I trial of an HLA-A1 restricted MAGE-3 epitope peptide with incomplete Freund's adjuvant in patients with resected high-risk melanoma. *J. Immunotherapy.* 22:431-440 (1999).

Wu et al., J. Immunol. 148:1519, (1992)

---

The invention claimed is:

1. A peptide vaccine, comprising:
an isolated signal peptide domain of MUC I consisting of an amino acid sequence MTPGT QSPFF LLLLL TVLTV V (SEQ ID NO. 10); and
a pharmaceutically acceptable carrier or diluent.

2. A pharmaceutical composition comprising: the peptide vaccine according to claim 1, or a nucleic acid vaccine comprising an isolated nucleic acid molecule consisting of a nucleotide sequence encoding the peptide according to claim 1, or an antigen presenting cell preloaded with the peptide vaccine of claim 1.

3. A pharmaceutical composition, comprising: the peptide vaccine according to claim 1, or a nucleic acid vaccine comprising an isolated nucleic acid molecule consisting of a nucleotide sequence encoding the peptide according to claim 1, or an antigen presenting cell preloaded with the peptide vaccine of claim 1.

4. A pharmaceutical composition, comprising: the peptide vaccine according to claim 1, or a nucleic acid vaccine comprising an isolated nucleic acid molecule consisting of a nucleotide sequence encoding the peptide according to claim 1, or an antigen presenting cell preloaded with the peptide vaccine of claim 1, wherein said pharmaceutically acceptable carrier or diluent is adapted for co-administration with one or more other antineoplastic agents.

5. A pharmaceutical composition comprising the peptide vaccine according to claim 1 for treating or inhibiting MUC1 expressing cancer.

6. The pharmaceutical composition according to claim 5, wherein said MUC1 expressing cancer is selected from the group consisting of colon cancer, gastric cancer, lung cancer, renal cell (RC) cancer, transitional cell (TC) cancer, prostate cancer, pancreatic cancer, breast cancer, ovary cancer, thyroid cancer, lymphoma, leukemia, and multiple myeloma (MM).

7. A method of treating or inhibiting cancer, comprising: administering a therapeutically effective amount of a pharmaceutical composition to a cancer patient in need thereof, the pharmaceutical composition comprising the peptide vaccine of claim 1, or a nucleic acid vaccine comprising an isolated nucleic acid molecule comprising a nucleotide sequence encoding the peptide vaccine of claim 1, or an antigen presenting cell preloaded with the peptide vaccine of claim 1.

8. The peptide vaccine according to claim 1, wherein the signal peptide has an amide at its C terminus.

9. The peptide vaccine according to claim 1, wherein the pharmaceutically acceptable carrier comprises one or more members selected from the group consisting of a solvent, a dispersion media, a coating, an antibacterial agent, an antifungal agent, an isotonic agent, an absorption enhancing agent, and a delaying agent.

10. The peptide vaccine according to claim 1, wherein the peptide elicits an antigen specific immune response.

11. The pharmaceutical composition according to claim 2, wherein the peptide elicits an antigen specific immune response.

12. A peptide vaccine, comprising:
an isolated signal peptide domain of MUC I consisting of an amino acid sequence MTPGT QSPFF LLLLL TVLTV V (SEQ ID NO. 10); and
an adjuvant.

13. A method for enriching a T cell population in vitro, comprising administering the peptide vaccine of claim 1 in vitro to said T cell population, whereby an enriched T cell population responsive to the peptide vaccine is obtained.

* * * * *